(12) United States Patent
Lai

(10) Patent No.: US 8,048,634 B2
(45) Date of Patent: Nov. 1, 2011

(54) CANCER SCREENING METHOD

(75) Inventor: Hung-Cheng Lai, Taipei (TW)

(73) Assignee: National Defense Medical Center, Taipei (TW)

( * ) Notice: Subject to any disclaimer, the term of this patent is extended or adjusted under 35 U.S.C. 154(b) by 3 days.

(21) Appl. No.: 12/543,400

(22) Filed: Aug. 18, 2009

(65) Prior Publication Data

US 2011/0045465 A1     Feb. 24, 2011

(51) Int. Cl.
*C12Q 1/68*     (2006.01)
(52) U.S. Cl. ...................................... 435/6.14; 435/6.18
(58) Field of Classification Search ........................ None
See application file for complete search history.

(56) References Cited

U.S. PATENT DOCUMENTS

2008/0311570 A1    12/2008   Lai

FOREIGN PATENT DOCUMENTS

TW           96102422      8/2008

OTHER PUBLICATIONS

Gronbaek et al, Modern Pathology 21 (5), 632 (2008).*
Izumi et al, Human Molecular Genetics 14 (8), 997 (2005).*
Peter C. Scacheri, Gregory E. Crawford, and Sean Davis; Article: Statistics for ChIP-chip and DNase Hypersensitivity Experiments on NimbleGen Arrays; Methods in Enzymology, vol. 411 pp. 270-282. Elsevier Inc. 2006.
Po-Hsuan Su, et al.; Presentation Title: Epigenomic analysis of DNMT3B-mediated cervical cancer invasion by methylated DNA immunoprecipitation identifies PTPRR as a metastasis suppressor gene; AACR Annual Meeting Apr. 22, 2009.

* cited by examiner

*Primary Examiner* — James Martinell
(74) *Attorney, Agent, or Firm* — WPAT, P.C.; Anthony King

(57) ABSTRACT

A method for screening cancer comprises the following steps: (1) providing a test specimen; (2) detecting the methylation rate of the CpG sequence in at least one target gene of the test specimen, wherein the target genes is consisted of PTPRR, ZNF582, PDE8B and DBC1; and (3) determining whether there is cancer or cancerous pathological change in the specimen based on the methylation rate in the target gene.

16 Claims, 4 Drawing Sheets

SEQUENCE LISTING

```
<160> NUMBER OF SEQ ID NOS: 24

<210> SEQ ID NO 1
<211> LENGTH: 5000
<212> TYPE: DNA
<213> ORGANISM: Homo sapiens

<400> SEQUENCE: 1
ggtcttcacc tgaagttgcc tgactacgtt gtctcagatt gatttcagaa ctgcattatc     60
```

```
agcagggcag ctgttgccta ctaacagtca tggaagtaga tctcagctgg gggatgatgg    120
ggaaacaaag agaagatag  ggacgaataa aggaaggaat ggggcacaga cagaaagaga    180
gagagagaaa agaaagaaag gaggagaggc aagagatagt gacctggggt ttcataccgc    240
ggtgggtggg agaaggagtg tgtgtggtgg gcgtatttct tcgtggtcag aatcaaagtc    300
agaactgacc tggggaacct gtgttcaaga cctgaacctg gaccagaagc caagggaaag    360
agaaagttgc ccaagaaaaa agggagaaat ttccaccagg cgaaaataga aatcgctgac    420
tgggtttgtg gctggagagc tgtccgtggt gctgactcct cctcattggg attccagtga    480
aggctgagaa gctctgcact ggctgctcct cctctccctt tcctctcccc tcagtcctga    540
ccttctgaga cccaggatca ttctggctag ctcgatgtct tctcctctct ttctcccttt    600
ctctttgtcg attaaataat ttttcccgag ttcccagttc atcactcaaa catttctctt    660
ccattttgtt tcaagactcc tcttcctcca attagttcac tggctcctag attgttctag    720
gcctccctgg tggtcacatc tctctcttat catcctttga attaaaaaac aaacaaaaaa    780
catacaatgg caatcataaa agcagacaac atgcactgag cactcactag gtgtcaggga    840
gcagtctaag tgcctttgca tacattaact catgagcagt ctaagtgcct ttgcatatat    900
taactcatta caattccaca tcaaccctat tagatgggta gatatattat tattctatta    960
aacagacaag gaattgaggc ttaaggggta agtgatttca ccaagaccag acagctacag   1020
gactccaacc tctctggagc ctgcacttct actgaatctg gctcttttac atattccaac   1080
accttttcct atgacttcct gcccctccat ctggtagcct taatgctttc tattcttgcc   1140
taatcttcag gggactaggg atctgcattg ctgatttggt ttaaatcaga agggaagcaa   1200
agtaaacaaa cataccaaat gtgcgctgtg tgggaattat catacgaggg ctttatttc    1260 tgcttcagga agaggcccta tgttagcagc cccagcctgc attcaggctg attgcagagt   1320
attttgcttt ttattttcat gtcttagtcc ctgtaccctc gcccctttcc cgcctctggt   1380
ggtctccaga gaacttcgtg tcccctcagc ttctccctcc tacatcctgc ctacgtagag   1440
aagctcttgc ttcattctgg gaggttacgt gggctctcgc ctacacaccg agagaaacaa   1500
acagtgtcaa acactcacag agagacgcgc agacacaaac ggacccacac gggcaactcc   1560
cgagacaaaa cccacactcg atggatccac gcggccgtgg aaacacctgc cgccccagaa   1620
acactcaggt actcgcgaca cacacagtac agtcacgctt aagggcacca ggattccggg   1680
tttgcgcgta tgcgcggtcc ctttggatgc tcgtgcgcat agacacaaca ccctacacgc   1740
cccagaccca cgaaactccc tacgctcag  cccagccca ccgggccgc  cttccctcg    1800 aggcggcctc ccgtctctcc tcctctcgct tctcctcctc ctccgcctaa agatgtacaa   1860
aacactcctc ggaagcaacc ccggcgttca gctcctccct ccccgccccc cggccgccgc   1920
tcccccattc attttcggcc gtcgccggct aagtccctcc ccggcgtag  cccggcctcc   1980 gccgctcccc gcccggagac cgcggcgcac ttggacttcc ctctccattc gccagccgcc   2040
tcgctcccgg accccacggc tgcaaactga tctggcgcgc ggggaggagg agagcgcagg   2100
cgagcgaacc cgcgagagag ggagagagcg agcgagcaac agcgagagcg agagcgagag   2160
agccgggagg cagagggagt agtgaccgcc ttccggagcc gggattcatg cctgtcctcg   2220
ggaccagcga aggggacttt acggctgagt atgagccagg ctgctaggag ccaggtaccc   2280
ccacgcctgc agtccccgcg ccgtgcccgg aatgcgagct gcacgcaggg ctctcccaag   2340
ttcccaccga gccgaataaa aagcgtcctc ccgcagctct ccgccaaaga cggacattga   2400
ctccaggtaa ggcggcgccg ggtgcagcgc cccgcagccc cgctgcccct tggacccggcc   2460
```

-continued

```
ccgggccgca ttcggggcgt ccccgcgctc ctctgcccct cccctaccg gcacccttgt      2520
ccgctcttca cctggccgcc ccgccgcctc caagtcttct ccagttctag ggaggggtt      2580
cctgtgcctg gggctcaaag ggctaattgc gggtttgagt gagtggcgtg tgtgtccccg     2640
cgcgctcccg acgtgtgcac catggtggga acttgatgtg gtgctagtgt gtttgcgtgt    2700
gcggcgtcgt ttgcgtttga tgcgtgtgtt cgtggtgtgt gtgtgtgtcc gtgtgtgtaa    2760
gggagggggtg aagagagaga ggtcctataa cctacttacg gcgcgatgtg tgtgtgcatg   2820
tttgtacgta tgtgtttgta tgtgtgccct cgtgtgtctt tttaattagg tctctccagc   2880
ttacacggaa tgggacccctt actataggat cacgtagtca ccgggaaacc cgctgtggac   2940
ttcctcttgg ggctctgggc ttggggttttg gggaggatta tggggctgta gatggcacct  3000
tatttagccc aatgttggta cgcttgaagg aaaattcctc caaacggtgg aatcctgcta    3060
cactgggacc cacagcttaa tatgaaagag acatggccaa cccccgaggc aaatgagacg   3120
ctgtcacttt aaattctaca ctgggcagac tccaagattc tgatgggaat ttggagacac   3180
tggatagtgg gtgacagaga aagggggaag tcagcggtgg gctccttatc tggggcttgg   3240
aaagtctggg atagggattt accctgcatc cccgtttgca atcaacagag cccctccggc   3300
ttctgttggt tttggggagg atctggcaag tttgcatgga tccccctcag gggaaaggag    3360
aaagcgtcct cggggacttg ctcatccatc acagttgcaa agggtctcag aggaaatttc   3420
atctggggcg gctgtggatg atatggaagg agatggatgg ggcactttcc taagacagat  3480
tcgtctttct ttccccattt caggcgggga agccccagaa gagtctctcc ctaaatatgc    3540
ctctccatgg ctcccctgga gttagggggga tattgagaga aggcagagag gtggagaggg  3600
agagagagag agcaagagcg agagagaggg agacagagag agagagtgtt tcagtactga   3660
gggagatcta caatttgaaa aggggctgtg agtgtggaac ccatgacaga atgtggcagt    3720
aattgactta aactgctgtc ggtttgcacc tcgcgtctct cacttggctc caaaatactg    3780
ccaagggcag ggggggcggtg gaggaatctc agccaggaag gtagtttggg tcaaggccct   3840
cttctcttctt cctccatct cctgggaggc tctttaggta ggtcccttgg ccaccctggc     3900
ttggtactgt tgggcttggg ctctggggcc agccattgat ttgattccca gctgcctctt   3960
aaaggcttgc cctactcagc aaaaatgctg agttttactg ctgttagcat ggcttccaga    4020
ctcggcagct gttactttct caaggtaagc ggcagccgtt ctgctctcag gcagggaggc    4080
taggagaaga caagggctgt gacgctggga cacagcctct tgtctagctc agcacggagg    4140
ggccgctgaa aagccctctt aggggaaaaa agtagaaata tatttggcct aaaaaatgta   4200
cacatatatt ctaggaagat atatatatat atatatatat caatcacaca cacacacaca   4260
cacacacatg tgttcatatt ctgggagag ataaaagcaa acatgtattt gtaggaacct    4320
gccctagtgg gtgggttcta cctgcaggca cttgcagaca taccattctc tgtccagagg   4380
ctgatacctc aggctgaagc cttcacatag ccacagaaa tctccttcag gaaactcatg    4440
tcagggcaga gctccctgga ttatcttggg tagggggtac tagggccaag gaggagaccc    4500
atttttggga actgcctcat tttctctctt tcctaattca cagacgatcg aaactggaag    4560
gaatattaaa gagcagaaag gcaggactct gtggcctaaa gagggaatga gaattcccca   4620
acattcagta gtgggttagt ggcatgccca ggactagaat ctaggcttat caatcagcta    4680
gatcaatacc cttttccactc ctcccagcaa tatacactct aggactgtat attgctccca   4740
cccctatctt gccaacctgc caccatgacc cctaccaaga caatcgcttg tcttccctca    4800
tcaaacttca cattttcaga gatgcatttc agggttttc tatctggaaa catggccctg    4860
```

| | | | | |
|---|---|---|---|---|
| aagagaaaag | atccaatgcc | tcaatcacta | ttcccgaaag | acacacacac acacacacac | 4920 |
| acacacacac | acacacacac | acacacacac | acacacacgg | tggtgggggg aggactgaga | 4980 |
| gagagacaga | gagagaacat | | | | 5000 |

<210> SEQ ID NO 2
<211> LENGTH: 5000
<212> TYPE: DNA
<213> ORGANISM: Homo sapiens

<400> SEQUENCE: 2

| | | | | | |
|---|---|---|---|---|---|
| agaacaactc | tgaagcatca | tcccaccttc | agaatcctcc | ctgcagggat gcctgaggct | 60 |
| tggtcaattt | ctccctctgc | tcaagcttgc | ctccctccat | tccctccctt tatttcctcc | 120 |
| cacaaatgtt | gactacaaga | gcacttccta | aaaagcctcc | ctctgcctgc taaacaccat | 180 |
| ctcagaatct | gcttctagga | ggacccaacc | tgtgcagaaa | ttttatgagc aatttgcctg | 240 |
| tccattaaaa | aatacagcat | agactttttc | caggttagct | ggagatggag ttttttttgta | 300 |
| tcaaaaaaag | agagctaaac | tgagaagaga | agcaaaggta | gaagaataag gttagactct | 360 |
| ccctgtataa | ctgaatttgg | gattgggaat | gatatcttgc | ttctctatga aatttagaaa | 420 |
| ctgtcttttg | aagtcttcat | ccagtcacat | ccaagagtgg | tccaggaaga aaaggaaaa | 480 |
| taagaatgaa | aaaaaacaa | aaaacaaacc | ttaaaattgg | atacttcttt gtgccttgca | 540 |
| ttaagcctct | atgttactgc | cctgtccgt | ataagcaact | ctagataaaa tcctttctta | 600 |
| gaccatctaa | tttatctccc | cgtgccattg | tgaaaatcgg | gcaggaatta ctgcgggaac | 660 |
| cagtgactga | atgggcagtg | gtgtctcgca | gctgtaactc | agagtttaca agggaaggat | 720 |
| gaacagcagc | catccttcta | aaggcattct | tcctctcctc | cagcacagct cagtctgtgc | 780 |
| atgcctcacc | aaggagaatg | agggaaggcc | ttgttgactg | cccagcccag agtgtgagga | 840 |
| acagcagttg | acatgggcgg | ctggacggga | tagaaaccag | catgaacatt tagtgacacc | 900 |
| taaggaagag | gtgaaaatgg | gggagaaagc | caagaaccat | cagacagctt ctttctgttc | 960 |
| ttgccttgga | tcttagggga | acgtatgtgt | tcaagggtgc | cttcctccgc agggcctccc | 1020 |
| atcccttggc | acaaacttcc | aaacgatgag | tagacatgga | atgggcttct tctgaagact | 1080 |
| gggtcaccat | ccaactcagc | cttcggagta | ggcggtgggg | ctggggaag aggacggaac | 1140 |
| catgaggtct | ctccatcact | tcccgggtgt | gttgagaggc | aagcaaatgc ggtgggtggg | 1200 |
| cctgggctgt | agggcccctg | ccatttcggg | aggggcctcc | tggtgtttag ctctgggatg | 1260 |
| tgtgaaaatg | tgttggtgaa | aagcgagagg | cttacacagc | ccttcagggg aagagggggct | 1320 |
| ggggcgctgg | gggcggcgtc | gggatgagtg | cagaagagac | gaggcctctg gacagcggag | 1380 |
| gaggagggga | gggcgccgag | gcgcggtgcc | agctgccgcg | cacaggggcc ccgcggcgga | 1440 |
| gccgagccgc | gggcacgctc | tgccctgtcg | ggagagctcc | gggagcggcg ggaggggcgg | 1500 |
| aggggcgcag | tggggcccgg | gcggctgcgg | ccgcggagcc | gggcacctg aggaggaagg | 1560 |
| agggtgggag | cgagggaggg | agggacggg | cgcagaccga | aagtgggaa agaaggtgca | 1620 |
| ggcaggcggg | caggcgggcg | ggcgccctgg | cccaggccg | cgggtgcggg agcccggcga | 1680 |
| ggtcgagctg | ggcggcggcg | ggggccgcgc | cgagggagga | ggggaaggcg gaggcgcggg | 1740 |
| gagcgtgttt | gggcgccgc | ggcggggagg | gtggcggccg | ctggtgcgcg cggggcgctg | 1800 |
| tgtatgcgcg | ctcccccgct | cggggaggaa | gatggcccaa | aagggaaagt tggggtgacg | 1860 |
| cgcgcggtcc | ccggaggctc | ggcggggggc | accggggcca | gccgacggga gcggcggaca | 1920 |
| cacaggccgg | ggggcgcgca | gtccgggcgc | cgccgcggcc | gcccctcac tgcaggtggc | 1980 |

-continued

```
agcgggtgcg ctgggtcccg gcggccgcgg gcgcgggcgg gcgcgcgggg gagcccggcc    2040
gagggatggg ctgcgccccc agcatccatg tctcgcagag cggcgtgatc tactgccggg    2100
actcggacga gtccagctcg ccccgccaga ccaccagcgt gtcgcagggc ccggcggcac    2160
ccctgcccgg cctcttcgtc cagaccgacg ccgccgacgc catcccccg agccgcgcgt    2220 cgggaccccc cagcgtagcc cgcgtccgca gggcccgcac cgagctgggc agcggtagca    2280
gcgcgggttc cgcagccccc gccgcgacca ccagcagggg ccggaggcgc cactgctgca    2340
gcagcgccga ggccgagact cagacctgct acaccagcgt gaaggtaaat gccccgcgct    2400
ggcacacgcc gtggggccg tccgccccgt cggcggggct cgcacgggta gggggctccg     2460
gcggagttgg gtgaccgtga ggcggttggt ttggagaggt tgtcactaag gaggagttta    2520
cttttcattt gtggagatga tgggagccca ggaaatgtgg tcagaaaaag gcccctggag    2580
gggtcctgga agcgtcctta gctggtcctg ggggactggg cggggaaggg agcgcagaag    2640
gaagcaggtg ggctggcctg ttcctccttg agggcaggaa ggctgtggct tggtttatgc    2700
aggaagaggg gtggggacca ttgagagcat tcggtggcca gtcctgttga atgaaatctg    2760
agcactgagc tggatttgcg tgccttgtag gtgactggtg cagttgcagc accaggatag    2820
atagtgcccc atattccgat ttttacctgg gattaccagc caggctggag tctcagcaca    2880
ggaaccgagc gtagggattt tgaatgaat gagtgttcgt gttttaagag atgtgggaac     2940
ggagcagagt ggaacctgtt gtttgtcact gtaacgtttc tctggttggg ctgcatccta    3000
gacagaattg agagaaccgg gccatgagtt cggagtgtca gcagagccac cgtgagggga    3060
cgtggtttcc agtgcagtac agctgtctga ggatgattct gcacatacaa ctgatcttcc    3120
cagagagtgg gattttgagg aagtggaaaa aattgtttag atggttaaag cagtcgctaa    3180
atatttattt cttaaagaca gaagaaaaat aattatttaa atagtgtcct cccgtatgtt    3240
ctcaaagtac cgttaaatcc aagaggcttt tcattgtgta aatctgggca ctgggtcttt    3300
tttcctttca gcaaacaaga taacaatggc atatcctatt gtacagagag aaaaaaatac    3360
tcctaatgtc agatagaatc acagccttta cctggtcaat aggttaccaa gaaccattcc    3420
atggattatt tgtcaaagac acatttgtat ttttaatagt taaaaacttg gtcttcattg    3480
gatgaaggca gcccacagtg gaggagtgag gagaaggata acatgttttg gcttcaatct    3540
ggaagtccaa aagttttta atgaacctat ttttttttta acagcatctg attgtttaac     3600
atgaagcttg actgatgttt gcttgtggtt gcagtgtttc tctggcagta atcataatca    3660
ccattatagt aaaaacatcg tttattgagc acctactatg tgccaggagt aagctttctc    3720
tcctaactat tgaatgttaa cagtgtgatc ttagcatagc atgtctgaag actagagtct    3780
aggatttatg acagtacaaa cctaccagtt gcccattcgt tacagaggca tgtgctgaac    3840
gctatacttt gcttttgtca agctctctct ctctcccct ccctgttcac acaaagttag     3900
ctttaggagc aattttcagg gatgaaaatg ttaaatttgg tgaaatatt aagttgggat     3960 attatcagta aagaccatcc ttttgcctga cggttgaaga cctgaagcag tagttcaaaa    4020
ttgtgacagc tcatgaactt tgtgatactt tttttggttg ctccagagaa attgtgaatt    4080 tttgtttctct agaatatcta taatctcagt ttagtacttg gcaactctag ctactccatg   4140
tttgttcagt agaagaaaga atactgaatg aacccattct gtacatttt aatacttccc     4200 tcaagaggct gcttagagac caaatgaagt aaaaactgaa gggacaatga gccccaatta    4260
ttagcagctt gtataaactt gtattaatct cattgctact tggcttaagt attaaaaggc    4320
ttgacctggg taggagttta actcattttg ctttatcaag aagattccca aataagagct    4380
```

```
taattcactc taacccatta ctgggaatgt tggaaatgaa accctggtt cattgactta    4440 acactacttt gcattgtgtg gatctcagaa agtatatatt tgaagtgaaa tttgagacca    4500 gagttatttta tgcaaatctt acagaattat tatcacagaa ctgccctaat atatttaata    4560 gtatccttttt aggcctgtga ctcggtgttg tattgtcttt tctcaatcgt aaagttcaca    4620
tgttctgtgc ccttttgttg ctgagataat tttataaaaa ctttacattc attttttttgt   4680 agactaagca ttcttttttt gccgtaagag tttgagatag ttgctaggca cgtggtggtg    4740
ccccacccct ttccaaagca cacaggtgga aaaataaaat ctttaccatt tggtcctgtt    4800
tacagtggtg gaaggttgta atagtttcca cccctcccc ctggccattt tacatcaatt     4860
atgaagtgta tcctcattat ctacttggcc tctggtattc cccagagtgc aaaaatgtgt    4920
gcttgatctc tctctctctc ttttctagca ataattcatc tcattaagct tttagaatga    4980
tgaggcatta tgatgtcaaa                                                 5000

<210> SEQ ID NO 3
<211> LENGTH: 5000
<212> TYPE: DNA
<213> ORGANISM: Homo sapiens

<400> SEQUENCE: 3
aagaaaaata gacctattgt aagtgggata caattatttt tccctaacct ccagccctgc      60
agcatttcta gtaacagatg ttagatgaga agagttattc ttctaagctt tacagaatgc     120
taaataaatt atctcaaagg ttgactcagt aagaatttca aagagttaat tgtcagtatt     180
gaactttgtc aactatcatt ttcatttatt cattttttgag tatctatttt gcatgaggca    240
ttgctctagg gagttgggac atatcaataa agtcatcaaa gttcttcaac attggagctc     300
aaattctgtt ttgcgggggg gagtagggaa atagatacta acaatagat tttataagta     360 attattttgg tttgttagaa agtgatacgg gaaaagcaaa ctggaggaca gtgaatcagg     420
aataggagaa gaggttgcag cttagagtgg tttgggatga aatgatagtg ccacagaaat     480
ggagtgtgcc acacgcatgg gggagtaggg ggtggagcac gttgctagag aggggctaga    540
catggagata tgtctctatt ttcagcagag aaggcctgtc aagatattaa aagtacatct     600
cattgtcccc ttctcccact tgttggagtg cttcctggcc ttgtctctca gagctgaaga    660
tgacataaat cataaaagaa ataaatggta ccgcctgggc tctctgatct tataaggtcc     720
cacctaattt aagctctggt ggatagccta tttcccatta gttgtctcaa ttcacagagg     780
atggagaaag aaagcactga atgagatgtg cagctcaact caatgggcac ttgttagccc    840
caattatttg gctaggacaa ctttattcaa gttaatggaa tacaaaactc agcagttctt     900
atggagactt caatgtgctg tagaacaaac cacagataaa tgaactgtct gaaagaataa     960
tatgaggcac ggctaaacaa gtgttgtgga agagaaagat cactgtaatc tagagttagt    1020
tagagttagg gctttctgga aaagtgagac caacattaca ccttcgaaaa ctagtgtggt    1080
ggtggtgcaa gtggaggaaa atgggaaaga ggcaacagtg tccataaaga cacagaggca    1140
gaaagggcag aggccctggg atagttaaaa gagaagtcta gctgagggac ttcttgactt    1200
gactagcagc aattagccat gactaataag gctttccaca ctccaaagac ttagatggag   1260
ggataaaaaa ccatctaatg gcagactgtg gtagcctccc tagagacaca gagctgggcc    1320
ggatgagtcc aggcactgac gtgatccatt atctttcacc ttaaagagta aagggaaac     1380 taaagttaat tacctccacg aaacaaaaag gtgccttctt gtgcttcaat tacatggata    1440
tattctacta gtctaaaagt atcttctcac ttctttctgt cactgtgagg acttgagtca    1500
```

-continued

```
gaagaaagtt taaatacagt cattgagctg gaaagagtgg aaagagaagc aaagaggggg      1560
aagctgtagg aaggacgaag tcaccccaa gatacatggt tactgcttac accaagcaag       1620
ctgccttggg aacgcttccc ccgagcagcc agaatgctca gcagtggaag acacctctat     1680
tcctgtaggc gagtcctggg aagctggtca atctgcaaat gccaattccc agcagtgagc     1740
tcggtccacg tgtaaatcaa gatttgggga aagagtaggg tgggtggcat ggttgacaat     1800
gtcatcagct ccctcctctg actcctgtgg tcgtgccccc atctactctc actcagctac     1860
accccacctt cggatttgtg atggacgctg ggtccctagt aaccacagca agtgtctccc     1920
ccgcacttcc cccttcccca ccccacccc caccccccaa caccacccca gcgatggagc      1980
ctactctgct ccaagccgcc gctaagaccc ggagaagcgg aatttcactt tgaaattccc     2040
ttgcctcgtg agggccggcg ctgggcatgc tcagtagccg cggcgctgct gctgggctgc     2100
tgggctggcg cggagtccac cctgccgtct ccgccttggc ttctgggcgt ccagaaggcc     2160
aggcatttgc cgcctctgag cgcttctgtt ccccttaccc gcaacctcct actgctcttc     2220
ctctctccct ctcttaggga ggttgaagct ggtgctggtt tctgtcggcg ccacagactg     2280
actgctctgc aaaccccagc cgaggacctg aatcccggag actagaagac ccttggcggt     2340
ggctctttct aatagcactt tacctgaagt ggggtcgtgg tggagtttct cctccacctc     2400
tcaatgcaaa cactatgcgg agagcagtct gcttccctgc gctgtgcctg ctccttaatc     2460
ttcacgctgc aggtaagggg ttgccaggct tagagccgga gctgtgcatg agatgggaaa    2520
ctgcacatgc ttaaggactc taggaaaagc ttgccttgcg aagaaagcct ttctaaaaag     2580
gtaaaacagg acagtacctg acagggaagg ggtgagggag tcgtgcacct gttggaaaac    2640
tgaggccgaa aacttaaccct aaaattagct cttgattttt ctttacttta tacgaaaata    2700
gtgaacattt tcaatatgaa tacaggtttg ctccccccttt cgcctcccct ccgtctagat    2760
tccctgctct tgtttctagg ctatgcactt aactgtcaat ttttcaggag agggataaga    2820
catcctgcta gatgtaacct tttctactgc agcggctact acattcataa ggtctcttgg    2880
tctagcgagc gctcatagga aggcattggc tgtaacctga tggaccacat ctccgcccaa    2940
aagatcgaaa tacatggttc acattagtga tgctgcacca ggctcctttg gcccctgctc    3000
ttgtcactcg aatttctaa gccaataaga ggaagaaaag gttttcaaata gaatcctctt    3060 gtctctttca gcaccgtggc tagcgtccgc tggcatatta aaaaaaaaaa aaaaaaaaa     3120 aaaaaaaaaa acaattacag ttccaaagct gacaaccctg ggttaggcac tgtccctcgg    3180
acagatttga taaggtgtaa ccaagagtaa cagtgagact gctcccaaat ataaatagat     3240
ttgaggcacc agaatcaata tcaagtctcg tgaggaagca aaccttggga agtacctgag    3300
agatattata tgtggtgtcc ctgcttttg catacatagc acctctattt aatgcagaca      3360
gacttgctag gctgaattcc ttatcattgt cacacacaca tgaaccaaaa taaatatgg     3420 cagggagatt ttagaaaccc tactgtgaca gcagttgtcc atgcagtagt cctgtaacaa    3480
ccagagacga ggcattttcc ctgagtgtgc ttctcatcca atcacacata tccattcatt    3540
ccttcaagca acatttgctg agtgtatact atgttctagg ggtaatgagt aaaaataatt    3600
gttctgaaat tacaatcctt gcagtatctt ttttaaaaga gtgggtgaat tttattctct    3660
gtgtacaata gtaggagtga aatatggtac tttcttattc cagctaacgc tattatttaa    3720
atgtatcatg aatcttttga gcaaataatg cataggatta ttaaagctat tattaaatac    3780
acatgttaat tgttataatt atgatgttat attgtggagt tttcaatagt tctttggcac    3840
attttgagaa gtagaaaata gctatgactt gattattaaa ttatttgcaa acagctgtag    3900
```

```
tgaattattt cgttaccaca tacaattctt caatgctgaa atgtgggatg aaaacataca    3960
cattgggttg agttttattt atagtattgc ttaataatag actgacacaa acattcatta    4020
cagaaaaatc tcaattctta ctaaggtagc aatgatttag ctggtctgcc aacaatatca    4080
gtgtagtcat ttttcaaaa ctaacatata aaaagttta aagatcacat ttgatacatc    4140
ttgagtaatt atatcttaaa agttataaat aaactgaagc atgtgaaaaa catgtcttga    4200
tttactgtag atgaatattc gggatgagaa aaatgaggac ttttgctcat cagatgagaa    4260
acctagaagc ctgtagccct agattttacc tggagttctg ccaaagggta tattaccaaa    4320
gccaatccaa tccatctcta cttcaacttt taatttgca aaacaaagat aaaaagtaag    4380
attaatcaac caattttaat ttaataagaa aatgcattta aggacatttt tatatttcaa    4440
ttgcaagata ctattcattg tattcatatt taatatagta aaatacattg gtgttttatc    4500
acagcagatt gtaagtttaa tattatagtt ctcttgccaa tttcatttta aatgcatttt    4560
aattttaaac agcaatttgt gggtcacaag ctgtcatcag attaaaattt atcacagtta    4620
tctaataaca ttgttagggc ttttcatcag aactaaaaca aacacagctc cttggtctaa    4680
gcttctatac atttggagat taagaaaata agtggatggg atgacaaaga tcaagaaatc    4740
aagatattaa tctctacttg ttgaaggtgt gagtttgtta cttttatgga agacttttct    4800
ctcagaacag aggctgactt cataaagaag ggaaatgaat tctatacatt caggcctctt    4860
taactgtaaa gctaattgat ccattttggt tacgcccagg gtatcagcaa ctgctttatg    4920
ctggtggaac tgatgacacc ttataatgct ttagagatgg gaggaatgtg ctaacgggat    4980
gtaagtgttc tttttagcta                                               5000
```

<210> SEQ ID NO 4
<211> LENGTH: 5000
<212> TYPE: DNA
<213> ORGANISM: Homo sapiens

<400> SEQUENCE: 4

```
gacgaccctg aatgatccct gcctcctagt acttatactc ttgtgtagcc tccacctact      60
tagactcaca gctgattttg tgaccaagag tataatggtg tatgacttca gaggcttggt     120
tcagagtcag aagtggccat ttcatcatcc tctaaatttc tctttggcag attaatgaat     180
gtgagaaagt aaaaatggta tagaagaaag ttagcctgag agatggctgg ctttgtacct     240
gtttggtctt tttccttcct ttcctccata agcaaatact gacgcatgta catatagaca     300
cactcaacac agtgggatgt aaagggaaa ctagagccac tcgcccttc caagatcag      360 agaacatagg aaagatgatg actttttgca tctaccctct cctcttgaac tcgcaacact     420
gtcttgaacc acaaataagg tcaagtagga taaatctaca actgtctcct caactgtccg     480
ctcacaagtg tgaaattcaa ccatccttgc tgaagttgtc ttttaatatc agtaatcagc     540
aataaccaac ctctgagctt tgcttatatt attaaatcat tttatttgac cctcaggaca     600
aagctgcaag cccagcatta cattcttcct tttatggaca aaaaaaaaa aacaaaacaa      660 aaccgagata ggcacgaaga aactaataaa tggctgaaat gctatttgaa tccacatctg     720
tctaattcta aaagtgtgct ttccaccaca tcaccgcacc tacaaggaaa atgcagcctc     780
taccctctcc tgaagaatgt gtaaagaggc aatatggtgt gttttggaaa aagcatcttt     840
gcagaaagaa agcattagct tcagtcatat tagcatcctt atccagcagc agtagcatta     900
ttttacatat cagttactcc tccccaacaa ctcaatgaat tagatgccac aatcatcctc     960
actttcaaat gtggagaccg aggcacatct ctaagactgg agttcaggca ttctggctcc    1020
```

```
agtcttagag atggttaagg gttcacactc ttaaccattt attacaccat agagctcacc   1080
aggtttgagg gaaacaggat caaatcaaaa gagtcactca ggactccagt cctcactcaa   1140
ggacaaactg ttccacctcg gacagggaga gtttccgcat tctgagaccc agcataacag   1200
gtcctgaccg gcatctggca ctcggactcc caatcatact ggatcacact ggctcgggat   1260
gtgtaaagtc cagggcttct cacatttgat gacaccaaag ccgcctaaaa acaagagaga   1320
attaacaact acctcggcg gtctgatatt tgcccaagag atgccgcccc ataaaactcc    1380
tttacatctt tataacgttt ttattttgcg ttctccttca taacccacat ttaactcacc   1440
atagatgtaa tgtttaaaat tagttaccag ataaactctt acgcttccaa actttaaggt   1500
tccttcgaaa ccttctggta aaactgttgt tccacggaaa tgggaacgta acggatgagg   1560
caatcttcca cagccgcaca cagttgtgta tccaccgcta acggtccca gtcatacatt    1620 caacgaccca cgcggagtca gaagctacca ccacacactg tcaaaatcac gcacacacag   1680
tgacggcccc ttgcccactc ggtcactcgc ccacaatctc tcgctagaga atcacacgca   1740
gatagcacac ccagcaccac agaccccagg aagcaaccca gggactcgaa cacacgaaca   1800
gcactcctcc gcgcactgcg caggcacgcc tgcgtccggc tcaccctgaa acatcgcgag   1860
atccggcttc aaggccgggc tgctgccttt acgcctaaag actatgtttc ccggaagaca   1920
ctgcggcgcc ggcccctatca tggcgcagca tcggtgtgct ttgtgcgtct gcgccatctt   1980
ccggctgcgc acggcgaatc caccggtacc gtggtggaag cgcgcccctgg gctgccgggg   2040 gcgcggccgc ggtggcactt ggacccgagg aggcggcagg tgagaggttc cggagctttc   2100
caggcgctct ggggtccagc aggagctggt gcccgggccg gttgggtctc aggcctgaga   2160
agaacgcaga cgtctcgcct catcgtcgct ctgtggcttt accggcgtga gactacattt   2220
cccgccggcc ctcgcggcgt gcgctttctg gcgccccctt tctgcttcca gcctcatagc   2280
ccaggtgcat ggacccctta ggtgggtgcg caggggtctc cgaccccctg aaattgcgga   2340
tgttttgcat tcactgttat gcgtgccttt ttttttttt aatctgagag gaaatcttgt    2400
ttcatgaggt tctcagagag ttacaagacc ccagaagact tagaaccgct agtttagaaa   2460
aacttatact tgggaacatt ttatatgttc aaattctatg tccagcaatg gggaaacact   2520
tgagtggatc acaggccatc ctttgtaaat aggatatcgt gcagttaata caaataatgc   2580
ttataaaagt ggtcataata aggaaaagct gcctattaca tcatattaag caacattcat   2640
aattatttca cttacacgtt acttagaacc aaatgtttgt aatgcagtag gcaccttata   2700
tactccttta cagagtactt cttgtttaac agtgagctca agaactggtt aaatgacaac   2760
actgcgaata cttgggtgtt ttttcttcca atttttttgt tttgttttgt tttagcctg    2820 tgtgttagta gtttgactt cttttttgctg aatgttctca aaggattcag tagttaatat   2880
ctttgcttgt cagttttga tagtcatttt tgatagtcac ttggcatccc attatatggc    2940
tgtgccaaaa atgattcaac ctcttggcta cttgtggact tgcctactta cgtactaatt   3000
ttcagttctc ctatttagca aatattattg gacatgcagc tttgtgcact gctgtgtctc   3060
tatggaagga cacattatg tgctgataat ggagcactgg gcgtgctgtg tgtaatttgt   3120
ctcttactgt tccttccaac tctatcccat ttgttgatgc aaggcatgct ccatgaagtg   3180
gcatgcacaa agcctcagtt tgggctgtag agctttttgt atatttggcg gttgggaaaa   3240
gagccaggta gactttcaaa ggtgttatat ttgctgcagg agagagttaa atggcctagt   3300
cctggaaagg ctttattcta ggctgggggct atgcaaatga tgcaggcctt ctatgctccc   3360
tggcttgagg gaagccctcc ttgtccttga ggtaacatgt gggtctcagt cactagaaca   3420
```

-continued

```
gccctcagca tccctgtctt agacttgcat ttgcagcaaa acagaaccac tggatgttta      3480
ggggaaatgg gagggaaagg accactggtt cccctttgcc ttgcagcagc taaagctggt      3540
ttcctggggt tgggtgagga tccctttgcc tccccctcct tctcatttc ttggtgggca       3600 gagggcaagc agtggggac ttgtaacttg gcattctagg aactgtgagg caagcctagc       3660
ctctcatgtt tgctctttcc tccccagct ctaccgtcgc aggactctgc ccttccccaa       3720
gagaggaacc agaaggagga cctatcagcc cttgaaattc taaaagtcat gtcccttgtg      3780 agttttaaa tcccataaat atttgctttc cttatcttga aactttccac ctgggttcca       3840
tccagaaatt tggttctcag actttcccat tttagggaat aaaaggacca ggcaggagtc      3900
tcctctccca ttgtcctctc ccctctgaca aatgcccaca gatttattct ctatagcatt      3960
ctgcatctcc tgatggtttt cgtctgctag gaggagaaac tcatttccct gtatgaaatg      4020
agagcatcct ttgtaagaac tgaagtttga agagatggaa tgaatgctta ggagcaatca     4080
catatagaaa agcaggggag gtggtgttgg ttggtttcag tttcagcgca tggtacagtg      4140
tcctgctttg ggaatgatta atgattggat atgtaattga ggtttggctg ggaatccatc     4200 aaaaattga tgccagaatt aaagtctagt ttgacgttgg acagagcatt tgaatctggg       4260
acatcctcca ttagtttctt tagcttaaga ggaagaaaag tacagagctg aggatggtga     4320
gcgatgtagc aagtgagatg atcatctagg tgggtgagtg gtcagggctt ggaaaagcct    4380
tagagatctg atccaacctc gggatccaaa ataagaggat gtttgagtca gttgtttcac    4440
ttgatagaaa attgtgcact caataaaagt tatctccatg gttttccca tgaagaaaaa     4500 tgcttgtgtt atgttccaac ataatgatga actttcatct ccaagaaatt cttgacttac    4560
atgaaaatcc tgtatctaag atagaaaaca tgttttccata attttaaaaa ataaaatatt    4620
tggggaaaat ccatcagaaa tattttttgt tgttattgtt attccaaaag atagaagtga     4680
taggtctcac cttgagaatt tattgtatgc caagtataga gtgggcagtg tgctttatta     4740 cactgttttct taacaataag gaaaactcca tttagcttga tttttaatttt catcccagac   4800 ctgtacacag agcattgatt tgcagttaaa aggaatgttt gagaacaatt tgatcattct     4860
gttttactca tccccatttc ttctgtcacc tttcacattc agtcccaccc ttcttgttca     4920
acaaaacaac cccccctccc gcaaagacct gccccatctc ctttcatccc actgtgaacc    4980
attgaaatac atatatatca                                                 5000
```

```
<210> SEQ ID NO 5
<211> LENGTH: 27
<212> TYPE: DNA
<213> ORGANISM: artificial sequence
<220> FEATURE:
<223> OTHER INFORMATION: forward primer

<400> SEQUENCE: 5
gttttcgtcg tttttcgttc ggagatc                                         27

<210> SEQ ID NO 6
<211> LENGTH: 25
<212> TYPE: DNA
<213> ORGANISM: artificial sequence
<220> FEATURE:
<223> OTHER INFORMATION: reverse primer

<400> SEQUENCE: 6
gctctcgctc tcgctattac tcgct                                           25

<210> SEQ ID NO 7
```

```
<211> LENGTH: 23
<212> TYPE: DNA
<213> ORGANISM: artificial sequence
<220> FEATURE:
<223> OTHER INFORMATION: forward primer

<400> SEQUENCE: 7
tgtgtatgcg cgttttttcg ttc                                              23

<210> SEQ ID NO 8
<211> LENGTH: 23
<212> TYPE: DNA
<213> ORGANISM: artificial sequence
<220> FEATURE:
<223> OTHER INFORMATION: reverse primer

<400> SEQUENCE: 8
acctatatat ccgccgctcc gtc                                              23

<210> SEQ ID NO 9
<211> LENGTH: 24
<212> TYPE: DNA
<213> ORGANISM: artificial sequence
<220> FEATURE:
<223> OTHER INFORMATION: forward primer

<400> SEQUENCE: 9
cggcgttggg tatgtttagt agtc                                             24

<210> SEQ ID NO 10
<211> LENGTH: 29
<212> TYPE: DNA
<213> ORGANISM: artificial sequence
<220> FEATURE:
<223> OTHER INFORMATION: reverse primer

<400> SEQUENCE: 10
aattacgaat aaaaaaaaca aaaacgctc                                        29

<210> SEQ ID NO 11
<211> LENGTH: 28
<212> TYPE: DNA
<213> ORGANISM: artificial sequence
<220> FEATURE:
<223> OTHER INFORMATION: forward primer

<400> SEQUENCE: 11
tgacggtttt ttgtttattc ggttattc                                         28

<210> SEQ ID NO 12
<211> LENGTH: 21
<212> TYPE: DNA
<213> ORGANISM: artificial sequence
<220> FEATURE:
<223> OTHER INFORMATION: reverse primer

<400> SEQUENCE: 12
cgaacgcaaa cgtacctacg c                                                21

<210> SEQ ID NO 13
<211> LENGTH: 26
<212> TYPE: DNA
<213> ORGANISM: artificial sequence
<220> FEATURE:
<223> OTHER INFORMATION: forward primer

<400> SEQUENCE: 13
```

```
ggttaagttt tttttttyggy gtagtt                                     26

<210> SEQ ID NO 14
<211> LENGTH: 26
<212> TYPE: DNA
<213> ORGANISM: artificial sequence
<220> FEATURE:
<223> OTHER INFORMATION: reverse primer

<400> SEQUENCE: 14
tactccctct acctcccrac tctctc                                      26

<210> SEQ ID NO 15
<211> LENGTH: 28
<212> TYPE: DNA
<213> ORGANISM: artificial sequence
<220> FEATURE:
<223> OTHER INFORMATION: forward primer

<400> SEQUENCE: 15
ttgtggygta gaggattatt agtttggt                                    28

<210> SEQ ID NO 16
<211> LENGTH: 22
<212> TYPE: DNA
<213> ORGANISM: artificial sequence
<220> FEATURE:
<223> OTHER INFORMATION: reverse primer

<400> SEQUENCE: 16
ctaaaaacrc aacccatccc tc                                          22

<210> SEQ ID NO 17
<211> LENGTH: 27
<212> TYPE: DNA
<213> ORGANISM: artificial sequence
<220> FEATURE:
<223> OTHER INFORMATION: forward primer

<400> SEQUENCE: 17 ggaatttat tttgaaattt ttttgtt                                      27

<210> SEQ ID NO 18
<211> LENGTH: 33
<212> TYPE: DNA
<213> ORGANISM: artificial sequence
<220> FEATURE:
<223> OTHER INFORMATION: reverse primer

<400> SEQUENCE: 18
ccccacttca aataaaatac tattaaaaaa aac                              33

<210> SEQ ID NO 19
<211> LENGTH: 30
<212> TYPE: DNA
<213> ORGANISM: artificial sequence
<220> FEATURE:
<223> OTHER INFORMATION: forward primer

<400> SEQUENCE: 19
tagtgayggt ttttgttta ttyggttatt                                   30

<210> SEQ ID NO 20
<211> LENGTH: 26
<212> TYPE: DNA
<213> ORGANISM: artificial sequence
<220> FEATURE:
```

<223> OTHER INFORMATION: reverse primer

<400> SEQUENCE: 20
taaacrtaaa aacaacaacc cracct  26

<210> SEQ ID NO 21
<211> LENGTH: 5000
<212> TYPE: DNA
<213> ORGANISM: unknown
<220> FEATURE:
<223> OTHER INFORMATION: bisulfite sequencing of DBC1

<400> SEQUENCE: 21

```
ggtttttatt tgaagttgtt tgattaygtt gttttagatt gattttagaa ttgtattatt      60
agtagggtag ttgttgttta ttaatagtta tggaagtaga ttttagttgg ggatgatgg      120
ggaaataaag agaaagatag ggaygaataa aggaaggaat ggggtataga tagaaagaga     180
gagagagaaa agaaagaaag gaggagaggt aagagatagt gatttggggt tttatatygy     240
ggtgggtggg agaaggagtg tgtgtggtgg gygtatttt tygtggttag aattaaagtt      300
agaattgatt tggggaattt gtgtttaaga tttgaatttg gattagaagt taagggaaag     360
agaaagttgt ttaagaaaaa agggagaaat ttttattagg ygaaaataga aatygttgat     420
tgggtttgtg gttggagagt tgttygtggt gttgattttt ttttattggg attttagtga     480
aggttgagaa gttttgtatt ggttgttttt tttttttttt tttttttttt ttagttttga     540
tttttgaga tttaggatta ttttggttag ttygatgttt tttttttttt tttttttttt      600
tttttgtyg attaaataat tttttygag ttttagttt attatttaaa tattttttt        660
ttatttgtt ttaagatttt ttttttttta attagtttat tggttttag attgttttag      720
gtttttttgg tggttatatt tttttttat tatttttga attaaaaaat aaataaaaaa       780
tatataatgg taattataaa agtagataat atgtattgag tatttattag gtgttaggga     840
gtagtttaag tgttttgta tatattaatt tatgagtagt ttaagtgttt ttgtatatat     900
taatttatta taatttata ttaatttat tagatgggta gatatattat tattttatta     960
aatagataag gaattgaggt ttaaggggta agtgatttta ttaagattag atagttatag    1020
gattttaatt tttttggagt ttgtattttt attgaatttg gttttttttat atattttaat   1080
attttttttt atgattttt gttttttat ttggtagttt taatgttttt tatttttgtt      1140
taatttttag gggattaggg atttgtattg ttgatttggt ttaaattaga agggaagtaa    1200
agtaaaataa tatattaaat gtgygttgtg tgggaattat tataygaggg ttttattttt    1260
tgttttagga agaggtttta tgttagtagt tttagtttgt atttaggttg attgtagagt    1320
attttgtttt ttatttttat gttttagttt ttgtatttty gttttttttt ygttttggt    1380
ggttttaga gaatttygtg ttttttagt tttttttttt tatattttgt ttaygtagag     1440
aagttttgt tttatttgg gaggttaygt gggtttygt ttatatatyg agagaaataa       1500
atagtgttaa atatttatag agagaygygt agatataaay ggatttatay gggtaatttt    1560
ygagataaaa tttatattyg atggatttay gyggtygtgg aaatatttgt ygttttagaa    1620
atatttaggt attygygata tatatagtat agttaygttt aagggtatta ggatttyggg    1680
tttgygygta tgygyggttt tttggatgt tygtgygtat agatataata ttttataygt     1740
tttagattta ygaaatttt tayggtttag ttttagttta ttygggtygt tttttttyg      1800
aggyggtttt tygttttttt tttttygtt tttttttttt tttygtttaa agatgtaaa      1860
aatattttty ggaagtaatt tyggygttta gtttttttt tttygtttt yggtygtygt     1920
```

```
tttttattt attttyggty gtygtyggtt aagtttttt  ttyggygtag ttyggtttty    1980
gtygttttty gttyggagat ygygygtat  ttggattttt ttttttatty  gttagtygtt    2040
tygttttygg attttayggt tgtaaattga tttggygygy  ggggaggagg agagygtagg    2100
ygagygaatt ygygagagag ggagagagyg agygagtaat agyagagyg  agagygagag    2160 agtygggagg tagagggagt agtgatygtt  tttyggagty gggatttatg tttgttttyg    2220
ggattagyga aggggatttt ayggttgagt atgagttagg ttgttaggag ttaggtatt    2280 ttaygtttgt agttttygyg tygtgttygg aatgygagtt gtaygtaggg ttttttttaag    2340 tttttatyga gtygaataaa aagygttttt tygtagtttt tygttaaaga yggatattga    2400
ttttaggtaa ggygygtyg ggtgtagygt ttygtagttt ygttgttttt ggattyggtt    2460
tygggtygta ttygggygt tttygygttt ttttgttttt ttttttatyg gtattttgt    2520 tygtttttta tttggtygtt tygtygtttt taagtttttt ttagttttag ggaggggtt    2580 tttgtgttg gggtttaaag ggttaattgy gggtttgagt gagtggygtg tgtgttttyg    2640
ygygttttyg aygtgtgtat tatggtggga attgatgtg  gtgttagtgt gtttygtgt     2700 gygygtgtygt ttgygtttga tgygtgtgtt ygtggtgtgt gtgtgtgtty gtgtgtgtaa    2760
gggaggggtg aagagagaga ggttttataa tttatttayg gygygatgtg tgtgtgtatg    2820
tttgtaygta tgtgtttgta tgtgtgtttt ygtgtgtttt tttaattagg ttttttttagt    2880 ttataygaa tgggattttt attataggat taygtagtta tygggaaatt ygttgtggat    2940 tttttttttgg ggtttgggt ttggggtttg gggaggatta tggggttgta gatggtattt    3000
tatttagttt aatgttggta ygtttgaagg aaaattttt  taaayggtgg aattttgtta    3060
tattgggatt tatagtttaa tatgaaagag atatggttaa ttttygaggt aaatgagayg    3120
ttgttatttt aaatttata ttgggtagat tttaagattt tgatgggaat ttggagatat    3180
tggatagtgg gtgatagaga aaggggggaag ttagyggtgg gttttttatt tggggtttgg    3240 aaagttggg atagggattt attttgtatt ttygtttgta attaatagag ttttttygtt    3300
ttttgttggt tttggggagg atttggtaag tttgtatgga tttttttag  gggaaaggag    3360 aaagygtttt yggggatttg tttatttatt atagttgtaa agggttttag aggaaatttt    3420
atttggggyg gttgtggatg atatggaagg agatggatgg ggtattttt  taagatagat    3480 tygttttttt ttttttattt taggyggga agttttaga gagttttttt ttaaatatgt     3540 tttttttatgg tttttttgga gttaggggga tattgagaga aggtagagag gtggagaggg    3600
agagagagag agtaagagyg agagagaggg agatagagag agagagtgtt ttagtattga    3660
gggagattta taatttgaaa aggggttgtg agtgtggaat ttatgataga atgtggtagt    3720
aattgattta aattgttgty ggtttgtatt tygygttttt tatttggttt taaaatattg    3780
ttaagggtag ggggygggtg gaggaatttt agttaggaag gtagtttggg ttaaggtttt    3840 ttttttttttt ttttttattt tttgggaggt ttttaggta ggtttttttgg ttattttggt    3900 ttggtattgt tgggtttggg ttttggggtt agttattgat ttgattttta gttgtttttt    3960
aaaggtttgt tttatttagt aaaaatgttg agttttattg ttgttagtat ggttttttaga    4020 ttyggtagtt gttattttttt taaggtaagy ggtagtygtt ttgtttttag gtagggaggt    4080
taggagaaga taagggttgt gaygttggga tatagttttt tgtttagttt agtayggagg    4140
ggtygttgaa aagtttttttt aggggaaaaa agtagaaata tatttggttt aaaaaatgta    4200
tatatatatt ttaggaagat atatatatat atatatatat taattatata tatatatata    4260
tatatatatg tgtttatatt ttggggagag ataaaagtaa atatgtattt gtaggaattt    4320
```

-continued

```
gttttagtgg gtgggtttta tttgtaggta tttgtagata tattattttt tgtttagagg    4380
ttgatatttt aggttgaagt ttttatatag ttatagagaa ttttttttag gaaatttatg    4440
ttagggtaga gttttttgga ttattttggg tagggggtat tagggttaag gaggagattt    4500 attttttggga attgttttat tttttttttt ttttaattta tagaygatyg aaattggaag    4560
gaatattaaa gagtagaaag gtaggatttt gtggtttaaa gagggaatga gaattttta     4620 atatttagta gtgggttagt ggtatgttta ggattagaat ttaggtttat taattagtta    4680
gattaatatt ttttttattt ttttagtaa tatatatttt aggattgtat attgttttta     4740
tttttatttt gttaatttgt tattatgatt tttattaaga taatygtttg tttttttta     4800 ttaaatttta tattttaga gatgtattt agggttttt tatttggaaa tatggttttg       4860
aagagaaaag atttaatgtt ttaattatta ttttygaaag atatatatat atatatatat    4920
atatatatat atatatatat atatatatat atatatatygg tggtgggggg aggattgaga   4980
gagagataga gagagaatat                                                 5000

<210> SEQ ID NO 22
<211> LENGTH: 5000
<212> TYPE: DNA
<213> ORGANISM: unknown
<220> FEATURE:
<223> OTHER INFORMATION: bisulfite sequencing of PDE8B

<400> SEQUENCE: 22
agaataattt tgaagtatta ttttattttt agaattttt ttgtagggat gtttgaggtt       60
tggttaattt ttttttttgt ttaagtttgt ttttttttat ttttttttt tattttttt      120 tataaatgtt gattataaga gtatttttta aaagtttttt ttttgtttgt taaatattat     180
tttagaattt gttttagga ggatttaatt tgtgtagaaa tttatgagt aatttgtttg       240 tttattaaaa aatatagtat agattttttt taggttagtt ggagatggag tttttttgta     300
ttaaaaaaag agagttaaat tgagaagaga agtaaaggta gaagaataag gttagatttt     360
ttttgtataa ttgaatttgg gattgggaat gatatttgt tttttttatga aatttagaaa    420 ttgttttttg aagttttat ttagttatat ttaagagtgg tttaggaaga aaaggaaaa      480 taagaatgaa aaaaaaataa aaaataaatt ttaaaattgg atatttttt gtgttttgta     540 ttaagttttt atgttattgt ttttgttygt ataagtaatt ttagataaaa tttttttta     600 gattatttaa tttattttt ygtgttattg tgaaaatygg gtaggaatta ttgyggaat      660 tagtgattga atgggtagtg gtgtttygta gttgtaattt agagtttata agggaaggat    720
gaatagtagt tattttttta aaggtatttt ttttttttt tagtatagtt tagtttgtgt     780
atgttttatt aaggagaatg agggaaggtt ttgttgattg tttagtttag agtgtgagga    840
atagtagttg atatgggygg ttggayggga tagaaattag tatgaatatt tagtgatatt    900
taaggaagag gtgaaaatgg gggagaaagt taagaattat tagatagttt ttttttgttt    960
ttgttttgga ttttaggga aygtatgtgt ttaagggtgt ttttttygt agggttttt      1020 attttttggt ataaatttt aaaygatgag tagatatgga atgggttttt ttgaagatt     1080 gggttattat ttaatttagt tttyggagta ggyggtgggg ttgggggaag aggayggaat    1140
tatgaggttt tttattatt tttygggtgt gttgagaggt aagtaaatgy ggtggtgggg    1200
tttgggttgt agggttttg ttatttyggg aggggtttt tggtgtttag ttttgggatg     1260
tgtgaaaatg tgttggtgaa aagygagagg tttatatagt tttttagggg aagagggtt    1320 ggggygttgg gggyggygty gggatgagtg tagaagagay gaggttttg gatagyggag    1380
```

```
gaggagggga gggygtygag gygyggtgtt agttgtygyg tataggggtt tygyggygga    1440
gtygagtygy gggtaygttt tgttttgtyg ggagagttty gggagyggyg ggaggggygg    1500 agggygygtag tggggttygg gyggttgygg tygyggagty ggggtatttg aggaggaagg   1560
agggtgggag ygagggaggg aggggayggg ygtagatyga aagtggggaa agaaggtgta    1620
ggtaggyggg taggyggggyg ggygttttgg tttagggtyg ygggtgyggg agttyggyga   1680
ggtygagttg ggyggyggyg ggggtygygt ygagggagga ggggaaggyg gaggygyggg    1740
gagygtgttt ggggygtygy ggygggggagg gtggyggtyg ttggtgygyg ygggyygttg   1800
tgtatgygyg ttttttygtt yggggaggaa gatggtttaa aagggaaagt tggggtgayg   1860
ygygyggttt tyggaggtty ggygggggggt atygyggtta gttygaygga gyggyggata   1920
tataggtygg ggggygygta gttygggygt ygtygggty gttttttttat tgtaggtggt    1980 agygggtgyg ttgggtttyg gyggtygygg gygygggygg gygygygggg gagttyggty    2040
gagggatggg ttgygttttt agtatttatg tttygtagag yggygtgatt tattgtyggg    2100
attyggayga gtttagttyg tttygttaga ttattagygt gtygtagggt tyggyggtat    2160
ttttgttygg ttttttygtt tagatygayg tygtygaygt tatttttttyg agtygygygt   2220 ygggattttt tagygtagtt ygygttygta gggttygtat ygagttgggt agyggtagta    2280
gygygggttt ygtagttty gtygygatta ttagtagggg tyggaggygt tattgttgta     2340
gtagygtyga ggtygagatt tagatttgtt atattagygt gaaggtaaat gtttygygtt    2400
ggtataygty gtgggggtyg ttygtttygt yggygggggtt ygtayggggta ggggggtttyg  2460 gyggagttgg gtgatygtga ggyggttggt ttggagaggt tgttattaag gaggagttta    2520
ttttttattt gtggagatga tgggagttta ggaaatgtgg ttagaaaaag gttttttggag   2580 gggttttgga agygttttta gttggttttg ggggattggg yggggaaggg agygtagaag    2640
gaagtaggtg ggttggtttg ttttttttttg agggtaggaa ggttgtggtt tggtttatgt   2700
aggaagaggg gtgggggatta ttgagagtat tyggtggtta gttttgttga atgaaatttg   2760
agtattgagt tggatttgyg tgttttgtag gtgattggtg tagttgtagt attaggatag    2820
atagtgtttt atatttygat ttttatttgg gattattagt taggttggag ttttagtata    2880
ggaatygagy gtagggattt gtgaatgaat gagtgttygt gttttaagag atgtgggaay    2940
ggagtagagt ggaatttgtt gtttgttatt gtaaygtttt tttgggttgg ttgtattta     3000 gatagaattg agagaatygg gttatgagtt yggagtgtta gtagagttat ygtgagggga    3060
ygtggttttt agtgtagtat agttgtttga ggatgatttt gtatatataa ttgatttttt    3120
tagagagtgg gattttgagg aagtggaaaa aattgtttag atggttaaag tagtygttaa    3180
atatttattt tttaaagata gaagaaaaat aattatttaa atagtgtttt ttygtatgtt    3240
tttaaagtat ygttaaattt aagaggtttt ttattgtgta aatttgggta ttgggttttt    3300 tttttttttta gtaaataaga taataatggt atatttatt gtatagagag aaaaaaatat    3360
ttttaatgtt agatagaatt atagttttta tttggttaat aggttattaa gaattatttt    3420
atggattatt tgttaaagat atatttgtat ttttaatagt taaaaatttg gtttttattg    3480
gatgaaggta gtttatagtg gaggagtgag gagaaggata atatgttttg gttttaattt    3540
ggaagtttaa aagttttta atgaattat tttttttttta atagtatttg attgtttaat    3600
atgaagtttg attgatgttt gtttgtggtt gtagtgtttt tttggtagta attataatta    3660
ttattatagt aaaaatatyg tttattgagt atttattatg tgttaggagt aagttttttt    3720
ttttaattat tgaatgttaa tagtgtgatt ttagtatagt atgtttgaag attagagttt    3780
```

```
aggatttatg atagtataaa tttattagtt gtttattygt tatagaggta tgtgttgaay    3840
gttatatttt gttttgtta  agttttttt  tttttttttt  ttttgtttat ataaagttag    3900
ttttaggagt aattttagg  gatgaaaatg ttaaatttgg tgaaaatatt aagtttgggat   3960
                                   
```

<210> SEQ ID NO 23
<211> LENGTH: 5000
<212> TYPE: DNA
<213> ORGANISM: unknown
<220> FEATURE:
<223> OTHER INFORMATION: bisulfite sequencing of PTPRR

<400> SEQUENCE: 23

```
aagaaaaata gatttattgt aagtgggata taattatttt ttttaatttt ttagttttgt      60
agtattttta gtaatagatg ttagatgaga agagttattt ttttaagttt tatagaatgt    120
taaataaatt attttaaagg ttgatttagt aagaatttta aagagttaat tgttagtatt    180
gaattttgtt aattattatt tttatttatt tattttgtag tattatttt gtatgaggta    240 ttgtttagg gagttgggat atattaataa agttattaaa gttttttaat attggagttt    300
aaattttgtt ttgygggggg gagtagggaa atagatatta ataatagat tttataagta    360 attatttggg tttgttagaa agtgataygg gaaaagtaaa ttggaggata gtgaattagg    420
aataggagaa gaggttgtag tttagagtgg tttgggatga aatgatagtg ttatagaaat    480
ggagtgtgtt ataygtatgg gggagtaggg ggtggagtay gttgttagag agggggttaga   540 tatggagata tgttttttatt tttagtagag aaggtttgtt aagatattaa agtatatttt    600
tattgttttt tttttttatt tgttggagtg tttttttggtt ttgttttta gagttgaaga    660 tgatataaat tataaaagaa ataaatggta tygtttgggt ttttgatttt tataaggttt    720
tatttaattt aagttttggt ggatagttta ttttttatta gttgtttta tttatagagg    780 atggagaaag aaagtattga atgagatgtg tagttaattt taatgggtat tgttagttt    840
```

```
taattatttg gttaggataa ttttatttaa gttaatggaa tataaaattt agtagttttt    900
atggagattt taatgtgttg tagaataaat tatagataaa tgaattgttt gaaagaataa    960
tatgaggtay ggttaaataa gtgttgtgga agagaaagat tattgtaatt tagagttagt   1020
tagagttagg gttttttgga aaagtgagat taatatttata ttttygaaaa ttagtgtggt   1080
ggtggtgtaa gtggaggaaa atgggaaaga ggtaatagtg tttataaaga tatagaggta   1140
gaaagggtag aggttttggg atagttaaaa gagaagttta gttgagggat ttttgattt    1200
gattagtagt aattagttat gattaataag gttttttata ttttaaagat ttagatggag   1260
ggataaaaaa ttatttaatg gtagattgtg gtagttttt tagagatata gagttgggty   1320
ggatgagttt aggtattgay gtgatttatt attttttatt ttaaagagta aaagggaaat   1380
taaagttaat tattttttayg aaataaaaag gtgtttttt gtgttttaat tatatggata   1440
tattttatta gtttaaaagt attttttat tttttttgt tattgtgagg atttgagtta    1500
gaagaaagtt taaatatagt tattgagttg gaaagagtgg aaagagaagt aaagaggggg   1560
aagttgtagg aaggaygaag ttattttaa gatatatggt tattgtttat attaagtaag   1620
ttgttttggg aaygtttttt tygagtagtt agaatgttta gtagtggaag atattttat    1680
ttttgtaggy gagttttggg aagttggtta atttgtaaat gttaattttt agtagtgagt   1740
tyggtttayg tgtaaattaa gatttgggga aagagtaggg tgggtggtat ggttgataat   1800
gttattagtt tttttttttg attttgtgg tygtgttttt atttatttt atttagttat    1860
attttatttt yggatttgtg atggaygttg ggttttagt aattatagta agtgtttttt   1920
tygtattttt ttttttttta tttttatttt tatttttaat tattatttta gygatggagt   1980
ttattttgtt ttaagtygty gttaagatty ggagaagygg aattttattt tgaaattttt   2040
ttgtttygtg agggtyggyg ttgggtatgt ttagtagtyg yggygttgtt gttgggttgt   2100
tgggttggyg yggagtttat tttgtygttt tygtttggt ttttgggygt ttagaaggtt   2160
aggtatttgt ygtttttgag ygtttttgtt tttttatty gtaattttt attgtttttt   2220
ttttttttt tttttaggga ggttgaagtt ggtgttggtt tttgtyggyg ttatagattg   2280
attgttttgt aaattttagt yggaggatttg aatttyggag attagaagat ttttggyggt   2340
ggtttttttt aatagtattt tatttgaagt ggggtygtgg tggagttttt tttttatttt   2400
ttaatgtaaa tattatgygg agagtagttt gtttttttgy gttgtgtttg tttttaatt   2460
tttaygttgt aggtaagggg ttgttaggtt tagagtygga gttgtgtatg agatgggaaa   2520
ttgtatatgt ttaaggattt taggaaaagt ttgtttttgyg aagaaagttt ttttaaaaag   2580
gtaaaatagg atagtatttg atagggaagg ggtgagggag tygtgtattt gttggaaaat   2640
tgaggtygaa aatttaattt aaaattagtt tttgatttt ttttatttta taygaaaata    2700
gtgaatattt ttaatatgaa tataggtttg ttttttttt ygtttttttt tygtttagat   2760
tttttgtttt tgtttttagg ttatgtattt aattgttaat ttttaggag agggataaga   2820
tattttgtta gatgtaattt ttttttattgt agyggttatt atatttataa gttttttgg   2880
tttagygagy gttatagga aggtattggt tgtaatttga tggattatat tttygtttaa    2940
aagatygaaa tatatggttt atattagtga tgttgtatta ggttttttg gtttttgttt   3000
ttgttattyg aattttttaa gttaataaga ggaagaaaag gttttaaata gaatttttt    3060
gttttttta gtatygtggt tagygttygt tggtatatta aaaaaaaaaa aaaaaaaaaa   3120
aaaaaaaaaa ataattatag ttttaaagtt gataattttg ggttaggtat tgttttyggg   3180
atagatttga taaggtgtaa ttaagagtaa tagtgagatt gttttaaat ataaatagat    3240
```

| | |
|---|---:|
| ttgaggtatt agaattaata ttaagttttyg tgaggaagta aattttggga agtatttgag | 3300 |
| agatattata tgtggtgttt ttgttttttg tatatatagt attttattt aatgtagata | 3360 |
| gatttgttag gttgaatttt ttattattgt tatatatata tgaattaaaa taaaatatgg | 3420 |
| tagggagatt ttagaaattt tattgtgata gtagttgttt atgtagtagt tttgtaataa | 3480 |
| ttagagayga ggtatttttt ttgagtgtgt tttttattta attatatata tttatttatt | 3540 |
| tttttaagta atatttgttg agtgtatatt atgttttagg ggtaatgagt aaaaataatt | 3600 |
| gttttgaaat tataatttt gtagtatttt tttaaaaga gtgggtgaat tttattttt | 3660 |
| gtgtataata gtaggagtga aatatggtat ttttttattt tagttaaygt tattatttaa | 3720 |
| atgtattatg aattttttga gtaaataatg tataggatta ttaaagttat tattaaatat | 3780 |
| atatgttaat tgttataatt atgatgttat attgtggagt ttttaatagt tttttggtat | 3840 |
| attttgagaa gtagaaaata gttatgattt gattattaaa ttatttgtaa atagttgtag | 3900 |
| tgaattattt ygttattata tataattttt taatgttgaa atgtgggatg aaaatatata | 3960 |
| tattgggttg agttttattt atagtattgt ttaataatag attgatataa atatttatta | 4020 |
| tagaaaaatt ttaattttta ttaaggtagt aatgatttag ttggtttgtt aataatatta | 4080 |
| gtgtagttat ttttttaaaa ttaatatata aaaagttta aagattatat ttgatatatt | 4140 |
| ttgagtaatt atattttaaa agttataaat aaattgaagt atgtgaaaaa tatgttttga | 4200 |
| tttattgtag atgaatatty gggatgagaa aaatgaggat ttttgtttat tagatgagaa | 4260 |
| atttagaagt ttgtagtttt agattttatt tggagttttg ttaaagggta tattattaaa | 4320 |
| gttaatttaa tttattttta ttttaatttt ttaatttgta aaataaagat aaaaagtaag | 4380 |
| attaattaat taattttaat ttaataagaa aatgtattta aggatatttt tatatttaa | 4440 |
| ttgtaagata ttatttattg tatttatatt taatatagta aaatatattg gtgttttatt | 4500 |
| atagtagatt gtaagtttaa tattatagtt ttttgttaa tttatttta aatgtatttt | 4560 |
| aatttaaat agtaatttgt gggttataag ttgttattag attaaaattt attatagtta | 4620 |
| tttaataata ttgttagggt ttttattag aattaaaata aatatagttt tttggttttaa | 4680 |
| gtttttatat atttggagat taagaaaata agtggatggg atgataaaga ttaagaaatt | 4740 |
| aagatattaa ttttatttg ttgaaggtgt gagtttgtta tttttatgga agatttttt | 4800 |
| tttagaatag aggttgattt tataaagaag ggaaatgaat tttatatatt taggtttttt | 4860 |
| taattgtaaa gttaattgat ttattttggt taygtttagg gtattagtaa ttgttttatg | 4920 |
| ttggtggaat tgatgatatt ttataatgtt ttagagatgg gaggaatgtg ttaaygggat | 4980 |
| gtaagtgttt ttttagtta | 5000 |

<210> SEQ ID NO 24
<211> LENGTH: 5000
<212> TYPE: DNA
<213> ORGANISM: unknown
<220> FEATURE:
<223> OTHER INFORMATION: bisulfite sequencing of ZNF582

<400> SEQUENCE: 24

| | |
|---|---:|
| gaygattttg aatgatttt gtttttagt atttatattt ttgtgtagtt tttatttatt | 60 |
| tagatttata gttgatttg tgattaagag tataatggtg tatgatttta gaggtttggt | 120 |
| ttagagttag aagtggttat tttattattt tttaaatttt ttttggtag attaatgaat | 180 |
| gtgagaaagt aaaaatggta tagaagaaag ttagtttgag agatggttgg ttttgtattt | 240 |
| gtttggtttt tttttttttt ttttttata agtaaatatt gaygtatgta tatatagata | 300 |

```
tatttaatat agtgggatgt taaagggaaa ttagagttat tygttttttt ttaagattag    360
agaatatagg aaagatgatg atttttttgta tttattttt tttttttgaat tygtaatatt    420 gttttgaatt ataaataagg ttaagtagga taaatttata attgtttttt taattgttyg    480
tttataagtg tgaaatttaa ttattttttgt tgaagttgtt ttttaatatt agtaattagt    540
aataattaat ttttgagttt tgtttatatt attaaattat tttatttgat ttttaggata    600
aagttgtaag tttagtatta tattttttt tttatggata aaaaaaaaaa aataaaataa    660
aatygagata ggtaygaaga aattaataaa tggttgaaat gttatttgaa tttatatttg    720 tttaattttta aaagtgtgtt ttttattata ttatygtatt tataaggaaa atgtagtttt    780 tattttttt tgaagaatgt gtaaagaggt aatatggtgt gttttggaaa aagtattttt    840
gtagaaagaa agtattagtt ttagttatat tagtatttt atttagtagt agtagtatta    900
ttttatatat tagttattttt tttttaataa tttaatgaat tagatgttat aattattttt    960 attttttaaat gtggagatyg aggtatattt ttaagattgg agtttaggta ttttggtttt   1020
agttttagag atggttaagg gtttatattt ttaattattt attatattat agagtttatt   1080
aggtttgagg gaaataggat taaattaaaa gagttattta ggattttagt ttttatttaa   1140
ggataaattg ttttatttyg gatagggaga gttttygtat tttgagattt agtataatag   1200
gttttgatyg gtatttggta ttyggatttt taattatatt ggattatatt ggttygggat   1260
gtgtaaagtt tagggttttt tatatttgat gatattaaag tygtttaaaa ataagagaga   1320
attaataatt atttayggyg gtttgatatt tgtttaagag atgtygtttt ataaaattt    1380 tttatattt tataaygttt ttattttgyg ttttttttta taattatat ttaatttatt    1440 atagatgtaa tgtttaaaat tagttattag ataaattttt aygttttttaa attttaaggt   1500 tttttygaaa tttttttggta aaattgttgt tttayggaaa tgggaaygta ayggatgagg   1560
taatttttta tagtygtata tagttgtgta tttatygtta aayggttttta gttatatatt    1620 taaygattta ygyggagtta gaagttatta ttatatattg ttaaaattay gtatatatag   1680
tgayggtttt tgtttatty ggttattygt ttataatttt tygttagaga attatyagta    1740
gatagtatat ttagtattat agattttagg aagtaattta gggattygaa tataygaata   1800 gtattttty ygtattgyg taggtaygtt tgygttyggt ttattttgaa atatygygag   1860
attyggtttt aaggtygggt tgttgttttt aygtttaaag attatgtttt tyggaagata   1920
ttgyggygty ggttttatta tggygtagta tyggtgtgtt ttgtgygttt gygttatttt    1980
tyggttgygt ayggygaatt tatyggtaty gtggtggaa ygygttttgg gttgtygggg    2040
gygyggtygy ggtggtattt ggattygagg aggyggtagg tgagaggttt yggagttttt   2100
taggygtttt ggggtttagt aggagttggt gttygggtyg gttgggtttt aggtttgaga   2160
agaaygtaga ygtttygttt tatygtygtt ttgtggtttt atyggygtga gattatattt    2220
ttygtyggtt ttygyggygt gygttttttg gygttttttt tttgttttta gttttatagt    2280
ttaggtgtat ggattttta ggtgggtgyg taggggtttt ygattttttg aaattgygga    2340
tgttttgtat ttattgttat gygtgttttt ttttttttt aatttgagag gaaatttgt    2400 tttatgaggt tttagagag ttataagatt ttagaagatt tagaatygtt agtttagaaa   2460
aatttatatt tggaatatt ttatatgttt aaatttatg tttagtaatg gggaaatatt    2520
tgagtggatt ataggttatt ttttgtaaat aggatatygt gtagttaata taaataatgt    2580
ttataaaagt ggttataata aggaaaagt gttattata ttatattaag taatatttat    2640
aattatttta tttataygtt atttagaatt aaatgtttgt aatgtagtag gtattttata   2700
```

```
tattttttta tagagtattt tttgtttaat agtgagttta agaattggtt aaatgataat    2760
attgygaata tttgggtgtt ttttttttta atttttttgt tttgttttgt ttttagtttg    2820
tgtgttagtg agtttgattt tttttttgttg aatgttttta aaggatttag tagttaatat   2880
ttttgtttgt tagtttttga tagttatttt tgatagttat ttggtatttt attatatggt    2940
tgtgttaaaa atgatttaat ttttggtta tttgtggatt tgtttattta ygtattaatt     3000
tttagttttt ttatttagta aatattattg gatatgtagt tttgtgtatt gttgtgtttt    3060
tatggaagga tatatttatg tgttgataat ggagtattgg gygtgttgtg tgtaatttgt    3120 ttttttattgt tttttttaat tttatttttat ttgttgatgt aaggtatgtt ttatgaagtg  3180
gtatgtataa agtttagtt tgggttgtag agttttttgt atatttggyg gttgggaaaa     3240
gagttaggta gattttttaaa ggtgttatat ttgttgtagg agagagttaa atggtttagt   3300
tttggaaagg ttttattttta ggttggggtt atgtaaatga tgtaggtttt ttatgttttt   3360
tggtttgagg gaagtttttt ttgtttttga ggtaatatgt gggttttagt tattagaata   3420
gtttttagta ttttttgtttt agatttgtat ttgtagtaaa atagaattat tggatgttta  3480
ggggaaatgg gagggaaagg attattggtt tttttttgtt ttgtagtagt taaagttggt   3540
tttttggggt tgggtgagga ttttttttgtt ttttttttttt ttttatttttt ttggtgggta 3600 gagggtaagt aggtggggat ttgtaatttg gtatttttagg aattgtgagg taagtttagt  3660
tttttatgtt tgttttttttt ttttttagtt ttatygtygt aggattttgt ttttttttaa  3720
gagaggaatt agaaggagga tttattagtt tttgaaattt taaaagttat gttttttgtg    3780 agttttttaaa ttttataaat atttgttttt tttattttga aattttttat ttgggtttta   3840
tttagaaatt tggttttttag atttttttat tttagggaat aaaaggatta ggtaggagtt   3900
ttttttttta ttgttttttt ttttttgata aatgtttata gatttattttt ttatagtatt   3960 ttgtattttt tgatggtttt ygtttgttag gaggagaaat ttattttttt gtatgaaatg   4020
agagtatttt ttgtaagaat tgaagtttga agagatggaa tgaatgttta ggagtaatta   4080
tatatagaaa agtaggggag gtggtgttgg ttggttttag ttttagygta tggtatagtg   4140
ttttgttttg ggaatgatta atgattggat atgtaattga ggtttggttg ggaatttatt   4200
aaaaatttga tgttagaatt aaagtttagt ttgaygttgg atagagtatt tgaatttggg   4260
atatttttta ttagttttttt tagtttaaga ggaagaaaag tatagagttg aggatggtga   4320
gygatgtagt aagtgagatg attatttagg tgggtgagtg gttagggttt ggaaaagttt   4380
tagagatttg atttaatttty gggatttaaa ataagaggat gtttgagtta gttgttttat   4440
ttgatagaaa attgtgtatt taataaaagt tattttttatg gttttttttta tgaagaaaaa  4500 tgtttgtgtt atgttttaat ataatgatga attttttattt ttaagaaatt tttgatttat   4560
atgaaaattt tgtatttaag atagaaaata tgttttttata attttaaaaa ataaaatatt   4620 tgggaaaat ttattagaaa tatttttttgt tgttattgtt attttaaaag atagaagtga    4680
taggttttat tttgagaatt tattgtatgt taagtataga gtgggtagtg tgttttatta   4740
tattgttttt taataataag gaaaattttta tttagtttga ttttaatttt tattttagat   4800
ttgtatatag agtattgatt tgtagttaaa aggaatgttt gagaataatt tgattatttt   4860 gttttatttta ttttttatttt ttttgttatt ttttatattt agttttattt ttttgttta   4920 ataaaataat ttttttttty gtaaagattt gttttatttt tttttatttt attgtgaatt   4980
attgaaatat atatatatta                                                5000
```

CANCER SCREENING METHOD

BACKGROUND OF THE INVENTION

1. Field of the Invention

The invention relates to the cancer screening method, cancer screening biomarker, and use thereof. In particular, to the cancer screening method using methylated DNA as the biomarker.

2. Description of the Prior Art

Cervical cancer has been one of the main causes of death in females worldwide and in Taiwan. Based on the statistical survey by the World Health Organization (WHO) in 2002, cervical cancer was the second major disease responsible for the death of women worldwide, second to breast cancer. Regular cervical cancer screening is the best way to prevent cervical cancer. Conventional cervical cancer screening includes two approaches: the most commonly used Pap smear, and human papilloma virus testing (HPV testing). Pap smear testing for early detection of cervical cancer consists of sampling secreta from cervix uteri then examining the sample under a microscope to determine whether there is cancerous pathological change in the exfoliated epithelial cell. On the other hand, HPV testing consists of examining whether human papilloma virus (HPV) is present in the specimen by using polymerase chain reaction (PCR) or Hybrid Capture.

There are, however, many undesired properties of Pap smear testing. For one, it requires sampling by a physician, and analysis by a medical examiner/pathologist, which has a high manpower cost that poses difficulty in promoting the test in many developing countries. Also, Pap smear has a high false negative rate which delays diagnosis and proper treatment prior to cancerous pathological change. As for HPV testing, although it is highly sensitive, it tends to create a high false positive rate, which not only makes patients worry in vain, but also wastes medical resources in follow up examinations resulting from those false positive patients. Accordingly, one of the important topics in promoting cervical cancer examination relies on increasing the accuracy and convenience of cervical cancer examination methods.

Genomic deletions have long been considered to be an important factor in tumorigenesis. For a long time, we have been accustomed to the idea that the coding potential of the genome lies within the arrangement of the four A, T, G, and C bases. The two-hit theory proposed as early as in 1970's indicates concomitant mutations or deletions of some homologous tumor suppressor genes may cause or predispose to cancer development. However, additional information that affects phenotype can be stored in the modified base 5-methylcytosine. 5-Methylcytosine is found in mammals in the context of the palindromic sequence 5'-CpG-3'. Most CpG dinucleotide pairs are methylated in mammalian cells except some areas called "CpG island." CpG islands are GC- and CpG-rich areas of approximately 1 kb, usually located in the vicinity of genes and often found near the promoter of widely expressed genes. Cytosine methylation occurs after DNA synthesis, by enzymatic transfer of a methyl group from the methyl donor S-adenosylmethionine to the carbon-5 position of cytosine. The enzymatic reaction is performed by DNA methyltransferases (DNMTs). DNMT1 is the main methyltransferase in mammals, and is responsible for the post-replicative restoration of hemi-methylated sites to full methylation, referred to as maintenance methylation, whereas DNMT3A and DNMT3B are thought to be involved primarily in methylating new sites, a process called isolated methylation.

Loss of methylation at CpG dinucleotides, i.e., general hypomethylation, was the first epigenetic abnormalities identified in cancer cells. However, during the past few years, it has become increasing apparent that site-specific hypermethylation, e.g., some tumor suppressor genes, is associated with loss of function which may provide selective advantages during carcinogenesis. Dense methylation of CpG islands at promoter regions can trigger chromatin remodeling through histone modifications with subsequent gene silencing. Therefore, in addition to chromosomal deletions or genetic mutations, epigenetic silencing of tumor suppressor genes by promoter hypermethylation is commonly seen in human cancer.

Epidemiologic studies have recently shown the correlation of serum folate level, a major source of methyl group, with the infection and clearance of HPV. Genetic polymorphisms of enzymes in the metabolism of methyl cycle were also reported to be associated with the development of cervical intraepithelial lesions. As the concept of epigenetics evolves, studies exploring the association between DNA methylation and cervical cancer are also booming. Studies of DNA methylation in cervical cancer are accumulating, which showed the potential of using methylation as markers in cervical screening. With the nature of the interface between genetics and environment, the prevalence of methylation in tumor suppressor genes varies in different genes and different populations. The concept of methylator phenotypes with different disease behaviors was proposed with controversy. The methylator phenotype of cervical cancer and its interaction with HPV genotypes still remains unknown. What genes are specifically methylated in cervical cancer and how many genes are required to achieve clinical application will remain a blossoming issue in the coming future.

The inventor of this application had filed relative patent applications in Taiwan (TW Pat. Pub. No. 200831900) and America (US Pat. Pub. No. 20080311570) (Hereinafter referred as prior applications). Comparing with prior applications, the inventor had found some novel cancer screening biomarker and cancer screening method using the same. Further, the research and development result of partial technology in this application had been disclosed publicly in AACR (American Association for Cancer Research) Annual Meeting 2009 held on Apr. 22, 2009.

SUMMARY OF THE INVENTION

One object of the invention is to provide a cervical cancer screening method as the first line cervical cancer screening.

Another object of the invention is to provide a cervical cancer screening method, characterized in that said method can be used not only in the first line cervical cancer screening, but also in the second line cervical cancer screening to assist HPV testing or uncertain smear result in order to achieve more accurate cervical cancer screening effect.

Yet another object of the invention is to provide a cancer screening method, characterized in that said method can be used in the screening of cervical cancer as well as in the screening of other cancer (for example: ovarian cancer, colon cancer and the like) to assist the diagnosis of abnormal specimen.

Another object of the invention is to provide the cancer screening biomarker, or a kit containing said biomarker to screen the risk of having cancer. The cancer screening method that can achieve the above-mentioned objects of the invention comprises of detecting the methylation rate of the target gene (biomarker) of the test specimen and use the testing result as a screening index to indicate the risk of having cancer, and said method comprises following steps:

step 1: providing an isolated test specimen;
step 2: detecting the methylation rate of CpG sequence in at least one target gene within the genomic DNA of said test specimen, wherein said target gene comprising DBC1, PDE8B, PTPRR and ZNF582; and
step 3: determining whether there is cancer or pre-cancerous pathological change or not in the specimen based on the methylation rate in the target gene, or using said methylation rate of target gene as prognosis marker;

wherein said test specimen comprising a cervical scraping, a ovarian cancer tissue, ascites, blood, urine, feces, sputum, oral mucous membrane cell, gastric juices, bile, cervical epithelial cell, and post-surgery cancer tissue;

wherein testing methods for the methylation state of CpG sequence in said target gene comprising methylation-specific polymerase chain reaction (MSP), quantitative methylation-specific polymerase chain reaction (QMSP), bisulfite sequencing (BS), microarrays, mass spectrometry, denaturing high-performance liquid chromatography (DHPLC);

wherein the target gene DBC1 has the nucleotide sequence as depicted in SEQ ID No: 1;
wherein the target gene PDE8B has the nucleotide sequence as depicted in SEQ ID No: 2;
wherein the target gene PTPRR has the nucleotide sequence as depicted in SEQ ID No: 3; and
wherein the target gene ZNF582 has the nucleotide sequence as depicted in SEQ ID No: 4.

In addition, the above-described screening index and screening method can be used further in the screening of cervical cancer, and colon cancer.

The invention provides further a ovarian cancer screening method, characterized in that said method tests the methylation state of the target gene of test specimen, and uses said methylation state as a screening index to determine the risk of having ovarian cancer, and said method comprises following steps:

step 1: providing an isolated test specimen;
step 2: detecting the methylation rate of CpG sequence in at least one target gene within the genomic DNA of said test specimen, wherein said target gene comprising DBC1, PTPRR and ZNF582; and,
step 3: determining whether there is ovarian cancer or cancerous pathological change or not in the specimen based on the methylation rate in the target gene, or using said methylation rate of target gene as prognosis marker;

wherein said test specimen comprising ovarian cancer tissue, ascites, blood, urine, and post-surgery cancer tissue;

wherein testing methods for the methylation state of CpG sequence in said target gene comprising methylation-specific polymerase chain reaction (MSP), quantitative methylation-specific polymerase chain reaction (QMSP), bisulfite sequencing (BS), microarrays, mass spectrometry, denaturing high-performance liquid chromatography (DHPLC), and pyrosequencing;

wherein the target gene DBC1 has the nucleotide sequence as depicted in SEQ ID No: 1;
wherein the target gene PTPRR has the nucleotide sequence as depicted in SEQ ID No: 3; and wherein the target gene ZNF582 has the nucleotide sequence as depicted in SEQ ID No: 4.

Term "test specimen" refers herein to isolated test specimen, and said isolated test specimen comprising the above-described cervical scraping, ascites, blood, urine, feces, sputum, oral mucous membrane cell, gastric juices, bile, cervical epithelial cell, post-surgery cancer tissue, or other suitable specimen. The inventive cancer screening method is useful to test the methylation state of target genes in said isolated test specimens, and uses said methylation state of biomarker as a screening index of various types of cancer. The cancer screening method and the screening index of biomarker provided by the invention can be employed by the researcher to perform the test in the laboratory.

Wherein, "the risk of having cancer" refers herein to the percentage of being cancer, the risk of getting cancer in future, or the presence or not of cancer.

Wherein when the methylation state of target gene (biomarker) being higher compare with suitable control, the risk of having cancer would be higher.

According to said screening method, the invention provides further the cancer screening biomarker or a kit containing said biomarker to screen the methylation state of target gene (biomarker) in isolated test specimen for determining the risk of having cancer.

These features and advantages of the present invention will be fully understood and appreciated from the following detailed description of the accompanying Drawings.

DETAILED DESCRIPTION OF THE PREFERRED EMBODIMENT

Figure 1A:
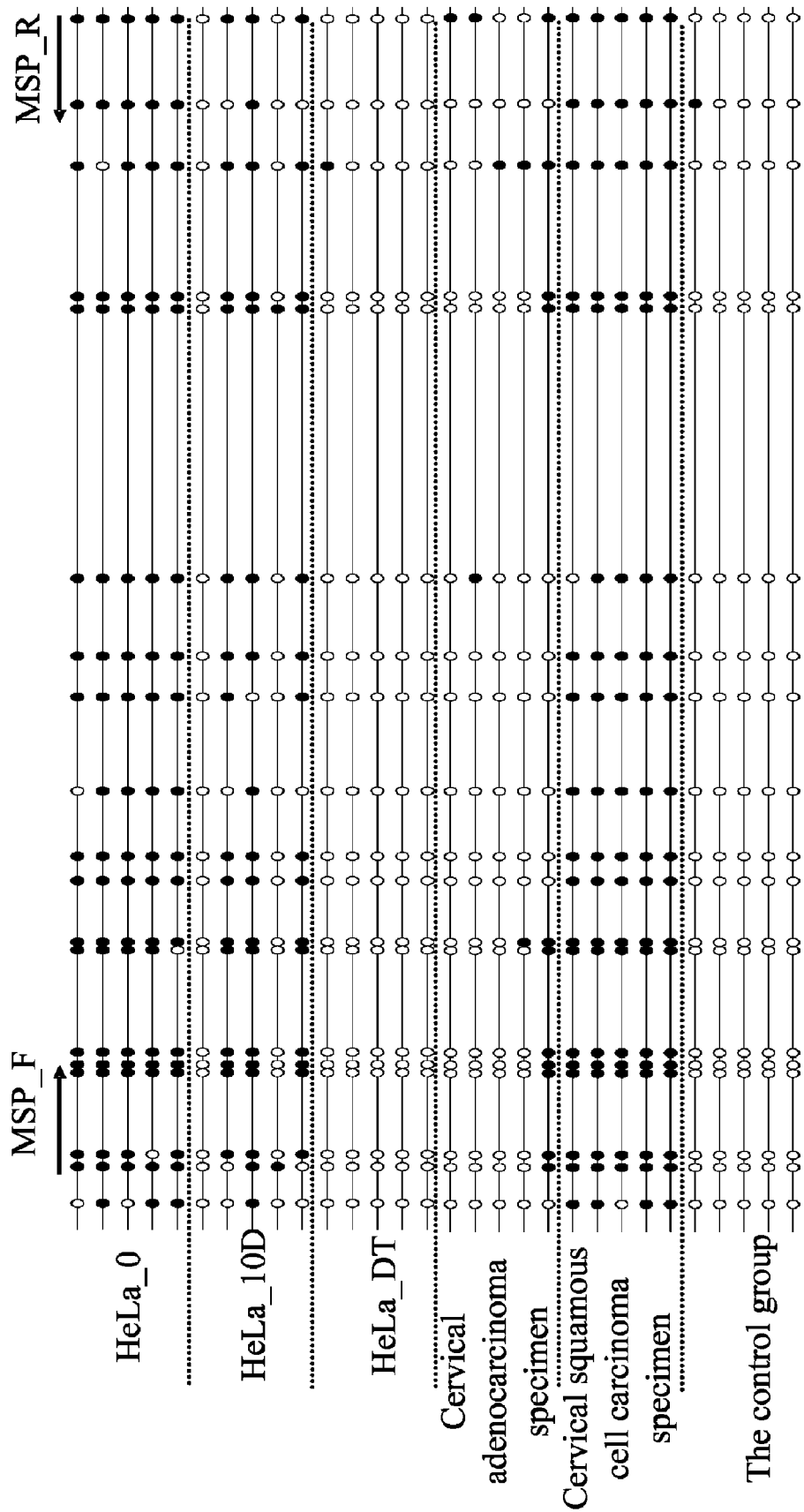
FIG. 1A shows the result obtained by performing bisulfite sequencing (BS) analysis on various cervical specimens using a target gene PTPRR in the inventive cancer screening method.

The invention will be illustrated more detailed with the following examples, but the invention is not limited thereto.

EXAMPLE 1

Materials and Methods

1. Materials

Test materials comprises a series of full cervical lesion specimens, including: squamous cell carcinoma (SCC, n=20), adenocarcinoma (AC, n=20), and normal cervical specimen (n=10). All of these cervical specimen, ovarian specimen, and colon cancer specimen were obtained from Tri-service General Hospital, Taipei, ROC. Each specimen was subjected to genomic DNA extraction by means of QIAamp DNA Kit (QIAGEN), and was used in the comparison and analysis of DNA methylation condition within genome-wide DNA methylation. Prior to the analysis, the quality of genomic DNA was checked by Bioanalyzer (Agilent). In this example, 10 µg of fragmented DNA was subjected to MeDIP (Methyl DNA IP) assay.

2. DNA Methylation Analysis by MeDIP and CpG Island-Plus-Promoter Arrays

Genomic DNA was fragmented to the size ranging from 300 to 1,000 bp by Bioruptor™ UCS-200 (Diagenode). It was immunoprecipitated overnight at 4° C. with 30 µl of polyclonal Anti-5'-methyl cytosine antibody (Abcam) in a final volume of 100 µl IP buffer (0.15% SDS, 1% Triton X-100, 150 mM NaCl, 1 mM EDTA, 0.5 mM EGTA, 10 mM Tris and 0.1% BSA). The mixture was then incubated with 120 µl of Protein G Sepharose (Amersham) for 2 hours at 4° C. and washed twice with 1 ml low salt, high salt buffer, lithium chloride and TE buffer. We then treated the protein G twice with elution buffer (1% SDS, 0.1M NaHCO$_3$) for 15 min at room temperature and recovered the Methylated DNA by phenol-chloroform extraction followed by ethanol precipitation. The enriched methylated DNA and input DNA were amplified by Whole Genome Amplification Kit (Sigma). Enriched and total DNA was end-labeled with Cy5 and Cy3, respectively, and co-hybridized to the CpG Island-Plus-Promoter Arrays designed and synthesized by NimbleGen Systems, Inc. This array contained 385,000 50-75 bp oligonucleotides tiled every 100 bp across the 24,659 HG18 RefSeq promoters (800 bp upstream to 200 bp down stream) and 28,226 CpG islands, present in duplicate.

Each feature on the array has a corresponding scaled log 2-ratio. The log 2-ratio is normalization to center the ratio data around zero. From the scaled log 2-ratio data, a fixed-length window (500 bp) is placed around each consecutive probe and the one-sided Kolmogorov-Smirnov (KS) test is applied to determine whether the probes are drawn from a significantly more positive distribution than those in the rest of the array. The resulting score for each probe is the −log 10 p-value from the windowed KS test around that probe (Scacheri et al, 2006). We detected enriched peaks by searching for at least 2 probes above a p-value minimum cutoff (−log 10) of 2. Peaks within 300 bp of each other are merged. Differential methylation regions between SCC/AC and normal cervix within 2500 bp upperstream of transcription star sites were selected for future validation. Finally, p-value data was viewed using SignalMap (NimbleGen).

3. Bisulfite Modification, Methylation-Specirific Polymerase Chain Reaction (MSP) and Bisulrite Sequencing (BS)

A DNA modification kit (Chemicon, Ternecula, Calif.) was used according to the manufacturer's recommendations to convert 1 µg aliquots of genomic DNA with sodium bisulfite to preserve the methylated cytosines. The final precipitate was eluted with 70 µl of pre-warmed (55° C.) TE buffer for MSP.

Normal DNA of human peripheral blood was taken and subjected to bisulfite modification, which was used as the control group having un-methylation promoter sequence.

MSP was performed according to prior art. In short, 1 µl of modified DNA was amplified using MSP primers (table 1) that specifically recognized the methylated gene sequences present in the bisulfite-converted DNA. Methylation-specific PCR was done in a total volume of 25 µl containing 1 µl of modified template DNA, 1.5 pmol of each primer, 0.2 mmol/L deoxynucleotide triphosphates, and 1 unit of Gold Taq DNA polymerase (Applied Biosystems, Foster City, Calif.). MSP reactions were subjected to an initial incubation at 95° C. for 5 minutes, followed by 35 cycles of 95° C. for 30 seconds, and annealing at the appropriate temperature for 30 seconds and at 72° C. for 30 seconds. The final extension was done at 72° C. for 5 minutes. Amplification products were visualized on 2.5% agarose gel containing ethidium bromide and illuminated under UV light.

TABLE 1

The sequences of MSP primers

| Gene | Primer | Sequence | |
|---|---|---|---|
| DBC1 | M Forward (F') | 5' gttttcgtcgtttttcgttcggagatc 3' | (SEQ ID No: 5) |
| | Reverse (R') | 5' gctctcgctctcgctattactcgct 3' | (SEQ ID No: 6) |
| PDE8B | M Forward (F') | 5' tgtgtatgcgcgttttttcgttc 3' | (SEQ ID No: 7) |
| | Reverse (R') | 5' acctatatatccgccgctccgtc 3' | (SEQ ID No: 8) |
| PTPRR | M Forward (F') | 5' cggcgttgggtatgtttagtagtc 3' | (SEQ ID No: 9) |
| | Reverse (R') | 5' aattacgaataaaaaaaacaaaaacgctc 3' | (SEQ ID No: 10) |
| ZNF582 | M Forward (F') | 5' tgacggttttttgtttattcggttattc 3' | (SEQ ID No: 11) |
| | Reverse (R') | 5' cgaacgcaaacgtacctacgc 3' | (SEQ ID No: 12) |

M: The primers can specifically recognize the methylated gene sequences present in the bisulfite-converted DNA.

All MSP data were derived from at least two independent modifications of DNA. The absence of signal in duplicate experiments was scored as negative methylation. PCR product obtained by using MSP primer (M) that can recognize specifically methylation gene sequence was constructed into a pCR4-TOPO vector (Invitrogen, Carlsbad, Calif.). Five independent clones were selected and were subjected to bisulfite sequencing (BS). Primers used in bisulfite sequencing (BS) were listed in Table 2. Bisulfite sequencing was carried out using 377 Auto-sequencer (Applied Biosystems, Foster City, Calif.). Sequenced results were shown in Sequence List. Sequence numbers in bisulfite sequencing were: DBC1_BS (SEQ ID No: 21), PDE8B_BS (SEQ ID No: 22), PTPRR_BS (SEQ ID No: 23) and ZNF582_BS (SEQ ID No: 24), respectively.

2. HeLa_10D: HeLa cervical cancer cell line (HeLa_0) treated with 10 μM DNA methyltransferase inhibitor 5'-aza-2'-deoxycytidine (AZC);

3. HeLa_DT: HeLa cervical cancer cell line (HeLa_0) treated with both of 10 μM DNA methyltransferase inhibitor 5'-aza-2'-deoxycytidine (AZC) and 0.33 μM TSA (Sigma Chemical Co., St. Louis, Mo.);

4. AC: Cervical adenocarcinoma specimen;

5. SCC: Cervical squamous cell carcinoma specimen; and

6. Control group (normal): normal cervical blood DNA as the control group without methylation.

TABLE 2

The sequences of bisulfite sequencing primers

| Gene | Primer | Sequence | |
|---|---|---|---|
| DBC1 | Forward (F') | 5'ggttaagttttttttyggygtagtt 3' | (SEQ ID No: 13) |
| | Reverse (R') | 5'tactccctctacctcccractctctc 3' | (SEQ ID No: 14) |
| PDE8B | Forward (F') | 5'ttgtggygtagaggattattagtttggt 3' | (SEQ ID No: 15) |
| | Reverse (R') | 5'ctaaaaacrcaacccatccctc 3' | (SEQ ID No: 16) |
| PTPRR | Forward (F') | 5'ggaattttattttgaaattttttttgtt 3' | (SEQ ID No: 17) |
| | Reverse (R') | 5'ccccacttcaaataaaatactattaaaaaaaac 3' | (SEQ ID No: 18) |
| ZNF582 | Forward (F') | 5'tagtgayggttttttgtttattyggttatt 3' | (SEQ ID No: 19) |
| | Reverse (R') | 5'taaacrtaaaaacaacaacccracct 3' | (SEQ ID No: 20) |

EXAMPLE 2

Screening of Methylated Target Gene in Cervical Cancer

After screened by CpG island-Plus-Promoter arrays, four target genes that might have been highly methylated in the cervical cancer cell were screened, namely, DBC1 (SEQ ID No: 1), PDE8B (SEQ ID No: 2), PTPRR (SEQ ID No: 3) and ZNF582 (SEQ ID No: 4), respectively. Their detailed information was shown in Table 3. It could be seen from Table 3 that, among these four genes, except DBC1 that was known to be associated with bladder cancer, little study up to date had revealed the relation of those genes to cervical cancer.

Each of those test specimens described above was subjected to bisulfite modification, and then bisulfite sequencing (BS) to analyze whether the target gene (PTPRR) in each test specimen has been hypermethylated or not. The results are shown in the Figure series 1, where black indicated methylation region, and white indicated un-methylation region. The target gene PTPRR had not been methylated in the control group and the adenocarcinoma, while the target gene PTPRR had been hypermethylated in HeLa cervical cancer cell line (HeLa_0) and cervical squamous cell carcinoma specimen (SCC). Consequently, the methylation rate of PTPRR could be used as biomarker to screen whether there was cervical cancer or not.

TABLE 3

Characteristics of methylated genes in cervical cancer that were identified using a CpG island-Plus-Promoter microarray.

| Gene | UniGene | Chromosomal location | Full name | SEQ ID No |
|---|---|---|---|---|
| DBC1 | NM_014618 | 9q32-q33 | deleted in bladder cancer 1 | SEQ ID No: 1 |
| PDE8B | NM_003719 | 5q14.1 | phosphodiesterase 8B | SEQ ID No: 2 |
| PTPRR | NM_002849 | 12q15 | protein tyrosine phosphatase, receptor type, R | SEQ ID No: 3 |
| ZNF582 | NM_144690 | 19q13.43 | zinc finger protein 582 | SEQ ID No: 4 |

EXAMPLE 3

The Analysis of Methylation State of Target Gene in Cervical Lesion Specimen by Bisulfite Sequencing (BS)

The Target Gene: PTPRR

Test Specimen Groups:

1. HeLa_0: HeLa cervical cancer cell line;

In addition, in order to ascertain whether methylation rate of the target gene in cervical cancer specimen could be regulated through DNA methylation, HeLa cervical cancer cell line was treated with 10 μM DNA methyltransferase inhibitor 5'-aza-2'-deoxycytidine (AZC) (Sigma Chemical Co.). The DNA specimen extracted from said cell was subjected to bisulfite modification and then bisulfite sequencing (BS). Result shown in FIG. 1A indicated that, compared with the cervical squamous cell carcinoma specimen (SCC) and HeLa cervical cancer cell line (HeLa__0), the target gene PTPRR in the AZC-treated HeLa cervical cancer cell line (HeLa__10D) had part of region been de-methylated.

Trichostatin A (TSA) is histone deacetylase (HDAC) inhibitors, and can be used to lower or degrade methylation rate. HeLa cervical cancer cell line (HeLa_DT) has been treated with both AZC and TSA. The result shown in FIG. 1A indicated that, compared with cervical squamous cell carcinoma specimen (SCC) and HeLa cervical cancer cell line (HeLa__0), the target gene PTPRR in the AZC- and TSA-treated HeLa cervical cancer cell line (HeLa_DT) had been highly de-methylated.

In summary, the above-described results had confirmed that the target gene PTPRR in cervical cancer specimen had been methylated through DNA methylation.

The Target Gene : ZNF582
  Test Specimen Groups:
  1. HeLa__0: HeLa cervical cancer cell line;
  2. HeLa__10D: the HeLa cervical cancer cell line (HeLa__0) treated with 10 μM DNA methyltransferase inhibitor 5'-aza-2'-deoxycytidine (AZC);
  3. HeLa_DT: the HeLa cervical cancer cell line (HeLa__0) treated with both of 10 μM DNA methyltransferase inhibitor 5'-aza-2'-deoxycytidine (AZC) and 0.33 μM TSA;
  4. SCC 1: Cervical squamous cell carcinoma specimen 1;
  5. SCC 2: Cervical squamous cell carcinoma specimen 2;
  6. The control group (normal): normal cervical blood DNA as the un-methylation control group;
  Wherein cervical squamous cell carcinoma specimen 1 and specimen 2 were specimens obtained from different patients.

Figure 1B:
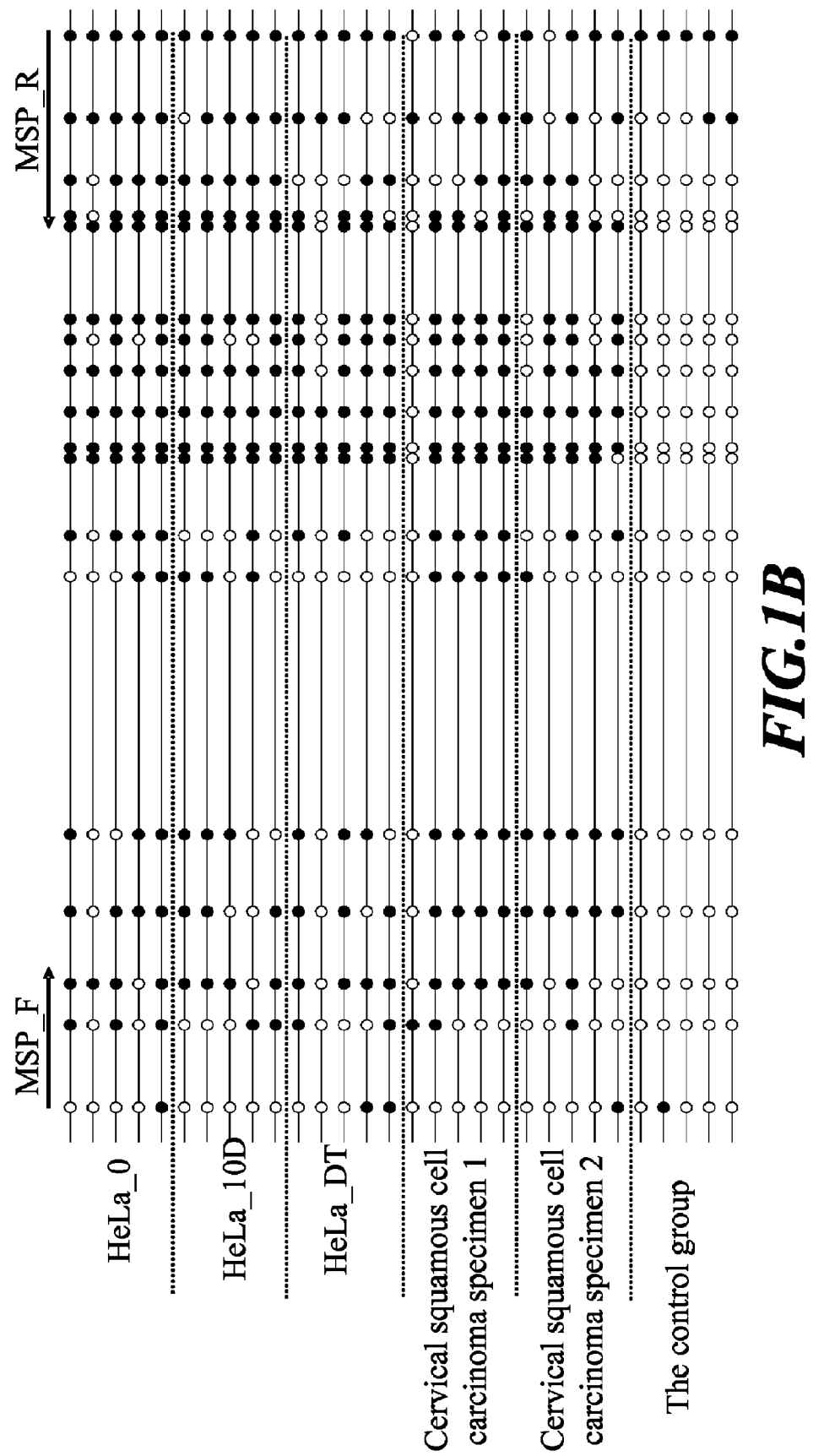
FIG. 1B shows the result obtained by performing bisulfite sequencing (BS) analysis on various cervical specimens using a target gene ZNF582 in the inventive cancer screening method.

Those test specimens mentioned above were subjected to bisulfite sequencing (BS) to analyze whether the target gene (ZNF582) in each test specimen had been hypermethylated or not. The result shown in FIG. 1B indicated that, compared with the control group, the target gene ZNF582 in cervical squamous cell carcinoma specimen 1 (SCC), cervical squamous cell carcinoma specimen 2 (SCC) and HeLa cervical cancer cell line (HeLa__0) had been hypermethylated. Consequently, the target gene ZNF582 in cervical cancer specimens would be highly methylated.

The Target Gene : PDE8B
  Test Specimen Groups:
  1. SiHa__0: SiHa cervical cancer cell line;
  2. SiHa__10D: SiHa cervical cancer cell line (SiHa__0) treated with 10 μM DNA methyltransferase inhibitor 5'-aza-2'-deoxycytidine (AZC);
  3. SiHa_DT: SiHa cervical cancer cell line (SiHa__0) treated with both of 10 μM DNA methyltransferase inhibitor 5'-aza-2'-deoxycytidine(AZC) and 0.33 μM TSA;
  4. SCC 1: Cervical squamous cell carcinoma specimen 1;
  5. SCC 2: Cervical squamous cell carcinoma specimen 2;
  6. The control group (normal): normal cervical blood DNA used as un-methylation control group;
  wherein cervical squamous cell carcinoma specimen 1 and specimen 2 were specimens obtained from different patients.

Figure 1C:
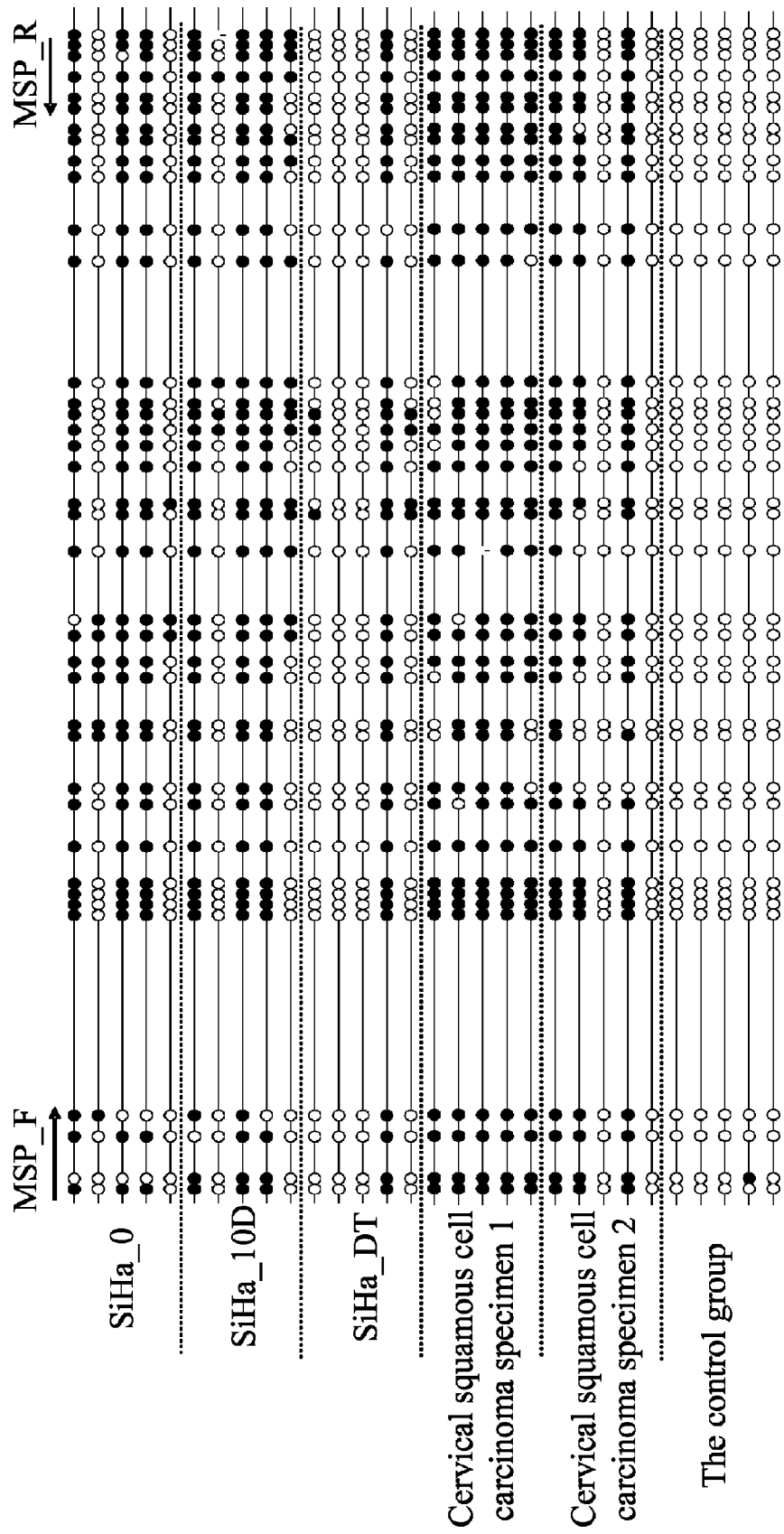
FIG. 1C shows the result obtained by performing bisulfite sequencing (BS) analysis on various cervical specimens using a target gene PDE8B in the inventive cancer screening method.

Those test specimens described above were subjected to bisulfite sequencing (BS) to analyze whether the target gene (PDE8B) in each test specimen had been hypermethylated or not. The result shown in FIG. 1C indicated that, compared with the control group, the target gene PDE8B in cervical squamous cell carcinoma specimen 1 (SCC 1), cervical squamous cell carcinoma specimen 2 (SCC 2) and SiHa cervical cancer cell line (SiHa__0) had been hypermethylated. Consequently, the target gene PDE8B in cervical cancer specimens would be highly methylated.

The Target Gene : DBC1
  Test Specimen Groups:
  1. SiHa__0: SiHa cervical cancer cell line;
  2. SiHa__10D: SiHa cervical cancer cell line (SiHa__0) treated with 10 μM DNA methyltransferase inhibitor 5'-aza-2'-deoxycytidine (AZC);
  3. SiHa_DT: SiHa cervical cancer cell line (SiHa__0) treated with both of 10 μM DNA methyltransferase inhibitor 5'-aza-2'-deoxycytidine (AZC) and 0.33 μM TSA;
  4. SCC 1: Cervical squamous cell carcinoma specimen 1;
  5. SCC 2: Cervical squamous cell carcinoma specimen 2;
  6. The control group (normal): normal cervical blood DNA as the un-methylation control group;
  wherein cervical squamous cell carcinoma specimen 1 and specimen 2 were specimens obtained from different patients.

Figure 1D:
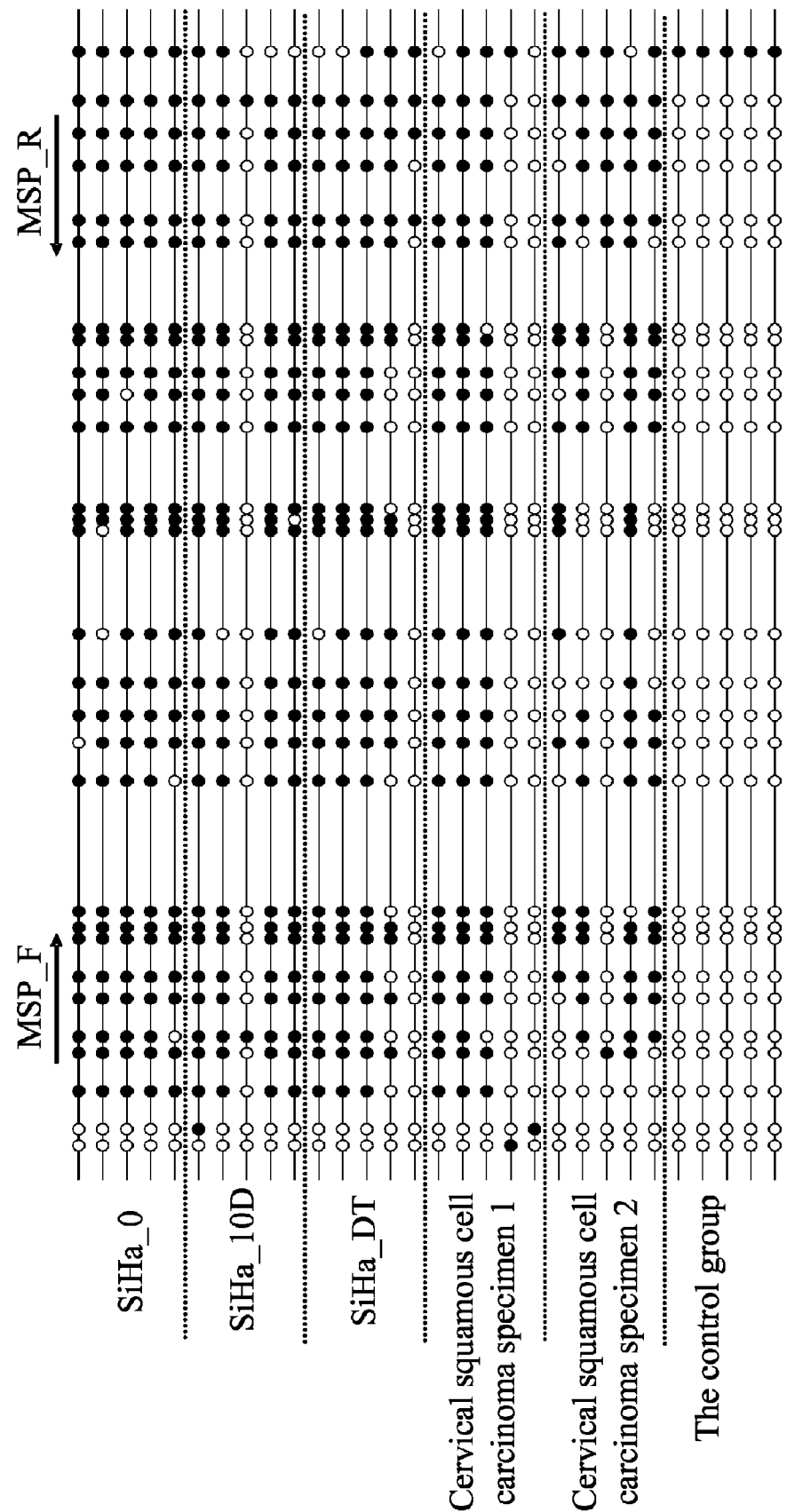
FIG. 1D shows the result obtained by performing bisulfite sequencing (BS) analysis on various cervical specimens using a target gene DBC1 in the inventive cancer screening method.

Those test specimens described above were subjected to bisulfite sequencing (BS) to analyze whether the target gene (DBC1) in each test specimen had been hypermethylated. The result shown in FIG. 1D indicated that, compared with the control group, the target gene DBC1 in cervical squamous cell carcinoma specimen 1 (SCC 1), cervical squamous cell carcinoma specimen 2 (SCC 2) and SiHa cervical cancer cell line (SiHa__0) had been hypermethylated. Consequently, the target gene DBC1 in cervical cancer specimens would be highly methylated.

EXAMPLE 4

Methylation Analysis of the Target Gene in Cervical Cancer Specimens

Methylation-specific PCR (MSP) was used to analyze the methylation state of said four target genes in cervical squamous cell carcinoma (SCC) specimens. The methylation state analysis result shown in Table 4 indicated that, in normal cervical specimen, methylation frequency of DBC1, PDE8B, PTPRR and ZNF582 was 11%, 0%, 9% and 6%, respectively; in cervical squamous cell carcinoma specimen, the methylation frequency of DBC1, PDE8B, PTPRR and ZNF582 was 100%, 47%, 100% and 97%, respectively. It could be known from these results that, in cervical squamous cell carcinoma specimens, said four genes were highly methylated. Consequently, methylation rate of DBC1, PDE8B, PTPRR and ZNF582 could be used indeed as the screening index in screening cervical cancer.

TABLE 4

Methylation state analysis of the target gene in cervical squamous cell carcinoma specimens

| | Target Genes CGI methylation rate (%) | |
|---|---|---|
| | Normal (n = 54) | SCC tissue (n = 30) |
| DBC1 | 11% | 100% |
| PDE8B | 0% | 47% |
| PTPRR | 9% | 100% |
| ZNF582 | 6% | 97% |

EXAMPLE 5

Methylation Analysis of the Target Gene in Ovarian Tumor Specimen

Methylation-specific PCR (MSP) was used to analyze the methylation state of the target gene in ovarian tumor specimens. Methylation state analysis results in Table 5 reported the analysis of methylation states of three genes DBC1, PTPRR and ZNF582 in ovarian malignant tumor specimen and ovarian benign tumor specimen. The results indicated that, the methylation frequency of DBC1, PTPRR and ZNF582 in ovarian malignant tumor specimen was 50.3%, 50.0% and 56.3%, respectively; the methylation frequency of DBC1, PTPRR and ZNF582 in ovarian benign tumor specimen was 2.5%, 0.0% and 12.5%, respectively. The differential methylation level was 53.8%, 50.0% and 43.8%, respectively. Consequently, compared with ovarian benign tumor specimen, methylation levels of said three genes in ovarian malignant tumor specimen were remarkably higher. Therefore, methylation rate of DBC1, PTPRR and ZNF582 could be used indeed as the screening index in screening ovarian cancer.

TABLE 5

Methylation state analysis of the target gene in ovarian tumor specimens

|  | Malignance_Ov (n = 28) | Benign_Ov (n = 28) | Differential Methylation_level |
| --- | --- | --- | --- |
| DBC1 | 56.3% | 2.5% | 53.8% |
| PTPRR | 50.0% | 0.0% | 50.0% |
| ZNF582 | 56.3% | 12.5% | 43.8% |

EXAMPLE 6

Methylation Analysis of the Target Gene in Colon Cancer Specimen

Methylation-specific PCR (MSP) was used to analyze the methylation state of the target gene in colon cancer specimen. The methylation state analysis result in Table 6 reported the methylation state of four genes, DBC1, PDE8B, PTPRR and ZNF582, in colon cancer specimen. The result indicated that, methylation frequencies of DBC1, PDE8B, PTPRR and ZNF582 in colon cancer specimen was 100.0%, 100.0%, 100.0% and 100.0%, respectively; while methylation frequencies of DBC1, PDE8B, PTPRR and ZNF582 in normal colon tissue specimen were 25.0%, 25.0%, 25.0% and 25.0%, respectively. Consequently, compared with normal colon tissue specimen, methylation levels of said four genes in colon cancer specimen were remarkably higher. Therefore, methylation rates of DBC1, PDE8B, PTPRR and ZNF582 could be used indeed as the screening index in screening colon cancer.

TABLE 6

Methylation state analysis of the target gene in colon cancer specimen

| | Target Genes CGI methylation rate (%) | |
| --- | --- | --- |
| | Normal colon tissue specimen (n = 24) | Colon cancer specimen (n = 20) |
| DBC1 | 25% | 100% |
| PDE8B | 25% | 100% |
| PTPRR | 25% | 100% |
| ZNF582 | 25% | 100% |

The cancer screening method provided by the invention has following advantages over the above-described conventional techniques:

1. The cancer screening method, biomarker and use thereof, provided by the invention uses the methylation rate of a particular gene in a isolated specimen as the biomarker to determine the risk of having cancer, and as compared with conventional methods such as cervical scraping and human papilloma virus testing (HPV testing), both of sensitivity and specificity of the inventive cancer screening method are higher than those of the two above-described methods.

2. The cancer screening method, biomarker and use thereof, provided by the invention can be used not only as the first line cervical cancer screening, but also in combination with or assisting human papilloma virus testing (HPV testing) as the second line cervical cancer screening, so as to achieve more accurate cervical cancer screening effect.

3. The cancer screening method, biomarker and use thereof, provided by the invention can be applied on not only the screening of cervical cancer, but also on the screening of other cancer (for example: ovarian cancer, colon cancer and the like) to assist the diagnosis of abnormal specimen.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A cancer screening method, comprises the following steps:
   step 1: providing a test specimen;
   step 2: detecting the methylation state of CpG sequences in at least one target gene of said test specimen, wherein said target gene comprises at least one selected from the group consisting of PDE8B, PTPRR and ZNF582; and
   step 3: determining whether there is cancer or pre-cancerous pathological change or not in the specimen based on the methylation state in the target gene, or said methylation state of the target gene regarded as a prognosis marker.

2. A cancer screening method as recited in claim 1, wherein said test specimen is an isolated specimen selected from the group consisting of cervical scraping, ascites, blood, urine, feces, sputum, oral mucous membrane cell, gastric juices, bile, cervical epithelial cell, and post-surgery cancer tissue.

3. A cancer screening method as recited in claim 1, wherein the testing method for the methylation state of CpG sequence of said target gene comprises methylation-specific polymerase chain reaction (MSP), quantitative methylation-specific polymerase chain reaction (QMSP), bisulfite sequencing (BS), microarrays, mass spectrometry, denaturing high-performance liquid chromatography (DHPLC), and pyrosequencing.

4. A cancer screening method as recited in claim 1, the target gene PDE8B has the nucleotide sequence as depicted in SEQ ID No: 2, the target gene PTPRR has the nucleotide sequence as depicted in SEQ ID No: 3, and the target gene ZNF582 has the nucleotide sequence as depicted in SEQ ID No: 4.

5. A cervical cancer screening method, comprises the following steps:
   step 1: providing a test specimen;
   step 2: detecting the methylation state of CpG sequences in at least one target gene of said test specimen, wherein said target gene comprises at least one selected from the group consisting of DBC1, PDE8B, PTPRR and ZNF582; and
   step 3: determining whether there is cervical cancer or cancerous pathological change or not in the specimen based on the methylation state in the target gene, or said methylation state of the target gene regarded as a prognosis marker.

6. A cervical cancer screening method as recited in claim 5, wherein said test specimen is an isolated specimen selected from the group consisting of cervical scraping, blood, urine, cervical epithelial cell, and post-surgery cancer tissue.

7. A cervical cancer screening method as recited in claim 5, wherein the testing method for the methylation state of CpG sequence of said target gene comprises methylation-specific polymerase chain reaction (MSP), quantitative methylation-specific polymerase chain reaction (QMSP), bisulfite sequencing (BS), microarrays, mass spectrometry, denaturing high-performance liquid chromatography (DHPLC), or pyrosequencing.

8. A cervical cancer screening method as recited in claim 5, wherein said target gene DBC1 has the nucleotide sequence as depicted in SEQ ID No: 1, the target gene PDE8B has the nucleotide sequence as depicted in SEQ ID No: 2, the target gene PTPRR has the nucleotide sequence as depicted in SEQ ID No: 3, and the target gene ZNF582 has the nucleotide sequence as depicted in SEQ ID No: 4.

9. An ovarian cancer screening method, comprises the following steps:
   step 1: providing a test specimen;
   step 2: detecting the methylation state of CpG sequences in at least one target gene of said test specimen, wherein said target gene comprises at least one selected from the group consisting of DBC1, PTPRR and ZNF582; and
   step 3: determining whether there is ovarian cancer or cancerous pathological change or not in the specimen based on the methylation state in the target gene, or using said methylation state of the target gene regarded as a prognosis marker.

10. An ovarian cancer screening method as recited in claim 9, wherein said test specimen is an isolated specimen selected from the group consisting of ovarian cancer tissue, ascites, blood, urine, and post-surgery cancer tissue.

11. An ovarian cancer screening method as recited in claim 9, wherein the testing method for the methylation state of CpG sequence of said target gene comprises methylation-specific polymerase chain reaction (MSP), quantitative methylation-specific polymerase chain reaction (QMSP), bisulfite sequencing (BS), microarrays, mass spectrometry, denaturing high-performance liquid chromatography (DHPLC), and pyrosequencing.

12. An ovarian cancer screening method as recited in claim 9, wherein said target gene DBC1 has the nucleotide sequence as depicted in SEQ ID No: 1, the target gene PTPRR has the nucleotide sequence as depicted in SEQ ID No: 3, and the target gene ZNF582 has the nucleotide sequence as depicted in SEQ ID No: 4.

13. A colon cancer screening method, comprises the following steps:
   step 1: providing a test specimen;
   step 2: detecting the methylation state of CpG sequences in at least one target gene of said test specimen, wherein said target gene comprises at least one selected from the group consisting of DBC1, PDE8B, PTPRR and ZNF582; and
   step 3: determining whether there is colon cancer or cancerous pathological change or not in the specimen based on the methylation state in the target gene, or said methylation state of the target gene regarded as a prognosis marker.

14. A colon cancer screening method as recited in claim 13, wherein said test specimen is an isolated specimen selected from the group consisting of ascites, feces, blood, urine, and post-surgery cancer tissue.

15. A colon cancer screening method as recited in claim 13, wherein the testing method for the methylation state of CpG sequence of said the target gene comprises methylation-specific polymerase chain reaction (MSP), quantitative methylation-specific polymerase chain reaction (QMSP), bisulfite sequencing (BS), microarrays, mass spectrometry, denaturing high-performance liquid chromatography (DHPLC), or pyrosequencing.

16. A colon cancer screening method as recited in claim 13, wherein said target gene DBC1 has the nucleotide sequence as depicted in SEQ ID No: 1, the target gene PDE8B has the nucleotide sequence as depicted in SEQ ID No: 2, the target gene PTPRR has the nucleotide sequence as depicted in SEQ ID No: 3, and the target gene ZNF582 has the nucleotide sequence as depicted in SEQ ID No: 4.

* * * * *